(12) United States Patent
Bihari et al.

(10) Patent No.: US 9,872,939 B2
(45) Date of Patent: Jan. 23, 2018

(54) POLYCARBONATE COPOLYMER COMPOSITIONS FOR FORMING MOLDED MEDICAL ARTICLES WITH THIN WALLS

(71) Applicant: SABIC Global Technologies B.V., Bergen op Zoom (NL)

(72) Inventors: Malvika Bihari, Mount Vernon, IN (US); Jon Malinowski, Indianapolis, IN (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 136 days.

(21) Appl. No.: 14/896,860

(22) PCT Filed: Jun. 12, 2014

(86) PCT No.: PCT/US2014/042138
§ 371 (c)(1),
(2) Date: Dec. 8, 2015

(87) PCT Pub. No.: WO2014/201257
PCT Pub. Date: Dec. 18, 2014

(65) Prior Publication Data
US 2016/0121026 A1 May 5, 2016

Related U.S. Application Data

(60) Provisional application No. 61/994,458, filed on May 16, 2014, provisional application No. 61/835,092, filed on Jun. 14, 2013.

(51) Int. Cl.
*A61L 29/06* (2006.01)
*A61L 31/06* (2006.01)
(Continued)

(52) U.S. Cl.
CPC .............. *A61L 29/06* (2013.01); *A61L 31/06* (2013.01); *C08L 23/02* (2013.01); *C08L 63/00* (2013.01);
(Continued)

(58) Field of Classification Search
CPC .......... A61L 29/06; A61L 31/06; C08L 23/02; C08L 63/00; C08L 69/005;
(Continued)

(56) References Cited

U.S. PATENT DOCUMENTS

2011/0071261 A1  3/2011  Hoeks et al.
2014/0206041 A1  7/2014  Malinoski et al.

FOREIGN PATENT DOCUMENTS

CN  101087848 A  12/2007
WO  2013020004 A1  2/2013

OTHER PUBLICATIONS

Chinese Patent No. 101087848(A); Date of Publication: Dec. 12, 2007; Machine Translation; 21 Pages.
(Continued)

*Primary Examiner* — Michael C Miggins
(74) *Attorney, Agent, or Firm* — Cantor Colburn LLP

(57) ABSTRACT

Disclosed is a thin-walled article that can be used for medical applications. The medical article is molded from a thermoplastic composition. The composition comprises a poly(aliphatic ester)-polycarbonate copolymer, a mold release agent, and a gamma radiation stabilizer. The composition exhibits excellent melt flow rate, is amenable to thin wall injection molding, and has good transparency.

20 Claims, 6 Drawing Sheets

(51) Int. Cl.
    *C08L 23/02*         (2006.01)
    *C08L 63/00*         (2006.01)
    *C08L 69/00*         (2006.01)

(52) U.S. Cl.
    CPC ......... *C08L 69/005* (2013.01); *C08L 2203/02* (2013.01); *C08L 2205/025* (2013.01); *C08L 2205/03* (2013.01); *C08L 2205/035* (2013.01)

(58) Field of Classification Search
    CPC ........... C08L 2203/02; C08L 2205/025; C08L 2205/03; C08L 2205/035
    See application file for complete search history.

(56) References Cited

OTHER PUBLICATIONS

International Search Report for International Application No. PCT/US2014/042138; International Filing Date: Jun. 12, 2014; dated Oct. 31, 2014; 4 Pages.

Written Opinion of the International Searching Authority for International Application No: PCT/US2014/042138; International Filing Date: Jun. 12, 2014; dated Oct. 31, 2014; 7 Pages.

US 9,872,939 B2

POLYCARBONATE COPOLYMER COMPOSITIONS FOR FORMING MOLDED MEDICAL ARTICLES WITH THIN WALLS

CROSS REFERENCE TO RELATED APPLICATIONS

This application is a 371 of International Application No. PCT/US2014/042138, filed Jun. 12, 2014, which claims priority to U.S. Application Nos. 61/994,458, filed May 16, 2014, and 61/835,092 filed Jun. 14, 2013 which are incorporated herein by reference in their entirety.

BACKGROUND

The present disclosure relates generally to polycarbonate copolymer compositions that have a high flow rate, high ductility, and can be also formed into thin walled structures with desirable impact strength for various applications in the medical field. Molded articles and processes for forming and/or using such polycarbonate copolymer compositions are also disclosed herein.

Polycarbonates (PC) are synthetic engineering thermoplastic resins derived from bisphenols and phosgene, or their derivatives. They are linear polyesters of carbonic acid and can be formed from dihydroxy compounds and carbonate diesters or carbonyl halides, or by ester interchange. Polycarbonates are a useful class of polymers having many beneficial properties.

There is a need for polycarbonate materials that can be easily processed to form a molded article with thin walls without brittleness and/or cracking, unsightly surfaces, and/or poor flowability. Such materials should also be strong enough to not shatter or break during molding and normal use. It would be desirable for such polycarbonate materials to be suitable for various medical applications, i.e. have additional characteristics such as biocompatibility and non-toxicity.

BRIEF DESCRIPTION

Disclosed herein are articles formed from high flow ductile polycarbonate copolymer compositions. These compositions offer superior processing properties compared to standard polycarbonates. The articles molded from these polycarbonate copolymer compositions have thin walls, and are particularly useful for medical applications. Exemplary molded articles include blood bowls, safety syringes, tubing, bags for fluids, etc.

Disclosed in various embodiments herein are medical articles molded from a thermoplastic composition comprising: at least one poly(aliphatic ester)-polycarbonate copolymer; a mold release agent; and a radiation stabilizer. The thermoplastic composition has a melt flow rate of about 25 g/10 minutes or higher measured at 300° C., 1.2 kg load according to ASTM D1238; and a light transmittance of 80% or higher, and a haze of 1% or less, measured at 2.54 mm thickness according to ASTM D1003.

Disclosed in various embodiments herein is a medical article molded from a thermoplastic composition comprising: at least one poly(aliphatic ester)-polycarbonate copolymer; a mold release agent; and a radiation stabilizer. The thermoplastic composition has a melt flow rate of about 25 g/10 minutes or higher measured at 300° C., 1.2 kg load according to ASTM D1238; and a light transmittance of 80% or higher, and a haze of 1% or less, measured at 2.54 mm thickness according to ASTM D1003.

In embodiments, the article can have a wall with a thinnest thickness of 5 mm or less, 2 mm or less, 0.5 mm or less, or 0.3 mm or less.

The composition can include two poly(aliphatic ester)-polycarbonate copolymers, a first poly(aliphatic ester)-polycarbonate copolymer having a weight average molecular weight of from about 15,000 to about 25,000, and a second poly(aliphatic ester)-polycarbonate copolymer having a weight average molecular weight of 30,000 to about 40,000. The weight ratio of the first poly(aliphatic ester)-polycarbonate copolymer to the second poly(aliphatic ester)-polycarbonate copolymer can be from about 3:2 to about 20:1. In some specific embodiments, the first poly(aliphatic ester)-polycarbonate copolymer contains about 6.0 mole % sebacic acid, and the second poly(aliphatic ester)-polycarbonate copolymer contains about 8.25 mole % sebacic acid.

The at least one poly(aliphatic ester)-polycarbonate copolymer can be derived from bisphenol-A and sebacic acid.

The at least one poly(aliphatic ester)-polycarbonate copolymer may have a biocontent of from about 4 wt % to about 10 wt %, measured according to ASTM D6866.

In some embodiments, the article distorts when autoclaved. The article may have a heat distortion temperature of 120° C. or less when measured at 1.82 MPa, 3.2 mm thickness according to ASTM D648, such that the article distorts when autoclaved. In other embodiments, the article has a heat distortion temperature of 121° C. or higher when measured at 1.82 MPa, 3.2 mm thickness according to ASTM D648.

The article may have a peak instrumented impact energy of 60 J or higher, when measured at 23° C. according to ASTM D3763. The article may have a notched Izod impact strength (INI) of 680 Joules per meter (J/m) or higher, when measured at 23° C. according to ASTM D256. The article may have a notched Izod impact strength (INI) of 450 J/m or higher, when measured at 0° C. according to ASTM D256.

The article may have both a notched Izod impact strength (INI) of 680 J/m or higher when measured at 23° C., and a notched Izod impact strength (INI) of 450 J/m or higher when measured at 0° C., according to ASTM D256.

Alternatively, the article may have both a notched Izod impact strength (INI) of 750 J/m or higher when measured at 23° C., and a notched Izod impact strength (INI) of 750 J/m or higher when measured at 0° C., according to ASTM D256.

The radiation stabilizer can be hexylene glycol. The mold release agent can be a polyalphaolefin.

Sometime, the thermoplastic composition further includes an epoxy resin.

The medical article may be non-implantable. Sometimes, the medical article is a blood bowl, disposable hypodermic syringe, needle shield, tubing/line, connector, needle wing, cannula, safety barrel, filter medium, sharps container, tray, injectable drug vial, prescription pill vial, inhaler part, IV drug or saline bag, blood bag, transfusion/retransfusion bag, irrigation solution bottle, fluid replacement bottle, nose spray bottle, packaging blister, surgical gown, isolation gown, isolation drape, sterilization wrap, or face mask. Alternatively, the medical article is a housing for a medical device.

Also disclosed in embodiments herein is a medical article molded from a thermoplastic composition comprising: a first poly(aliphatic ester)-polycarbonate copolymer having a weight average molecular weight of from about 15,000 to about 25,000; a second poly(aliphatic ester)-polycarbonate copolymer having a weight average molecular weight of 30,000 to about 40,000; a mold release agent; a radiation stabilizer; and an epoxy resin; wherein the weight ratio of the first poly(aliphatic ester)-polycarbonate copolymer to the second poly(aliphatic ester)-polycarbonate copolymer is about 3:1; and wherein the thermoplastic composition has a melt flow rate of about 25 g/10 minutes or higher when measured at 300° C., 1.2 kilogram (kg) load according to ASTM D1238; a light transmittance of 80% or higher, and a haze of 1% or less, measured at 2.54 mm thickness according to ASTM D1003; a heat distortion temperature of 120° C. or less when measured at 1.82 megaPascals (MPa), 3.2 millimeters (mm) thickness according to ASTM D648; a notched Izod impact strength (INI) of 750 J/m or higher when measured at 23° C., and a notched Izod impact strength (INI) of 750 J/m or higher when measured at 0° C., according to ASTM D256.

The first and second poly(aliphatic ester)-polycarbonate copolymers may each be derived from bisphenol-A and sebacic acid. The first poly(aliphatic ester)-polycarbonate copolymer can contain about 6.0 mole % sebacic acid, and the second poly(aliphatic ester)-polycarbonate copolymer can contain about 8.25 mole % sebacic acid.

In embodiments, the radiation stabilizer is hexylene glycol and the mold release agent is a polyalphaolefin. In more specific embodiments, the composition contains about 0.3 parts per hundred (phr of the mold release agent, about 0.1 phr of the radiation stabilizer, and about 0.1 phr of the epoxy resin.

Also disclosed is a medical article molded from a thermoplastic composition comprising: a first poly(aliphatic ester)-polycarbonate copolymer having a weight average molecular weight of from about 15,000 to about 25,000; a second poly(aliphatic ester)-polycarbonate copolymer having a weight average molecular weight of 30,000 to about 40,000; a mold release agent; a radiation stabilizer; and an epoxy resin; wherein the weight ratio of the first poly(aliphatic ester)-polycarbonate copolymer to the second poly(aliphatic ester)-polycarbonate copolymer is about 19:1; and wherein the thermoplastic composition has a melt flow rate of about 40 g/10 minutes or higher when measured at 300° C., 1.2 kg load according to ASTM D1238; a light transmittance of 80% or higher, and a haze of 1% or less, measured at 2.54 mm thickness according to ASTM D1003; a heat distortion temperature of 120° C. or less when measured at 1.82 MPa, 3.2 mm thickness according to ASTM D648; a notched Izod impact strength (INI) of 680 J/m or higher when measured at 23° C., and a notched Izod impact strength (INI) of 450 J/m or higher when measured at 0° C., according to ASTM D256.

The first and second poly(aliphatic ester)-polycarbonate copolymers can each be derived from bisphenol-A and sebacic acid.

The first poly(aliphatic ester)-polycarbonate copolymer can contain about 6.0 mole % sebacic acid, and the second poly(aliphatic ester)-polycarbonate copolymer can contain about 8.25 mole % sebacic acid.

In particular embodiments, the radiation stabilizer is hexylene glycol and the mold release agent is a polyalphaolefin. The composition can contain about 0.3 phr of the mold release agent, about 0.1 phr of the radiation stabilizer, and about 0.1 phr of the epoxy resin.

The composition may have a delta YI of 3 or less when measured at least 48 hours after exposure to 50 kGy of gamma radiation at 0.65 mm thickness.

The composition may have a multiaxial impact strength of at least 60 J when measured at least 48 hours after exposure to 50 kGy of gamma radiation at 3.2 mm thickness according to ASTM D3763.

The composition may have a tensile modulus of at least 2300 MPa when measured at least 48 hours after exposure to 25 kGy of gamma radiation at 3.2 mm thickness according to ASTM D638.

The composition may have a % elongation at break of at least 100% when measured at least 48 hours after exposure to 25 kGy of gamma radiation at 3.2 mm thickness according to ASTM D638.

Also disclosed is a process for preventing the reuse of a medical article molded from a thermoplastic composition, comprising: forming the medical article from a thermoplastic composition comprising: at least one poly(aliphatic ester)-polycarbonate copolymer; a mold release agent; and a radiation stabilizer; wherein the thermoplastic composition has a melt flow rate of about 25 g/10 minutes or higher measured at 300° C., 1.2 kg load according to ASTM D1238; and a light transmittance of 80% or higher, and a haze of 1% or less, measured at 2.54 mm thickness according to ASTM D1003; and wherein the article has a heat distortion temperature of 120° C. or less when measured at 1.82 MPa, 3.2 mm thickness according to ASTM D648. Here, preventing the reuse means the integrity of the medical article is not maintained for further use after the medical article is subjected to sterilization or autoclaving.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
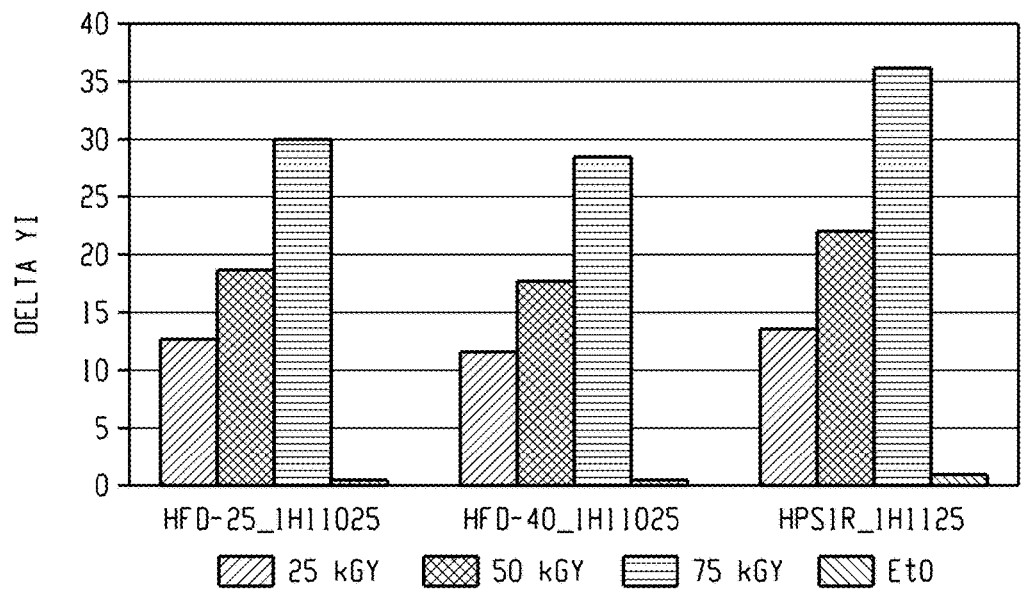
FIG. 1 is a graph illustrating the delta YI for various compositions exposed to different amounts of gamma radiation and to ethylene oxide sterilization for chip samples of 3.2 mm thickness.

The present disclosure may be understood more readily by reference to the following detailed description of desired embodiments and the examples included therein. In the following specification and the claims which follow, reference will be made to a number of terms which shall be defined to have the following meanings.

The singular forms "a," "an," and "the" include plural referents unless the context clearly dictates otherwise.

As used in the specification, various articles and compositions may be described as "comprising" other ingredients. The terms "comprise(s)," "include(s)," "having," "has," "can," "contain(s)," and variants thereof, as used herein, are intended to be open-ended transitional phrases, terms, or words that require the presence of the named ingredient and permit the presence of other ingredients. However, such description should be construed as also describing the devices and parts as "consisting of" and "consisting essentially of" the enumerated ingredients, which allows the presence of only the named component, along with any impurities that might result from the manufacture of the named component, and excludes other ingredients.

Numerical values in the specification and claims of this application, particularly as they relate to polymers or polymer compositions, reflect average values for a composition that may contain individual polymers of different characteristics. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

As used herein, approximating language may be applied to modify any quantitative representation that may vary without resulting in a change in the basic function to which it is related. Accordingly, a value modified by a term or terms, such as "about" and "substantially," are intended to include the degree of error associated with measurement of the particular quantity based upon the equipment available at the time of filing the application. The modifier "about" should also be considered as disclosing the range defined by the absolute values of the two endpoints. For example, the expression "about 2 to about 4" also discloses the range "2 to 4."

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, the aldehyde group —CHO is attached through the carbon of the carbonyl group.

Unless specifically specified otherwise, the date of the test standards set forth herein is the most recent date of the standard as of the date of the filing of this application.

The term "aliphatic" refers to a linear or branched array of atoms that is not cyclic and has a valence of at least one. Aliphatic groups are defined to comprise at least one carbon atom. The array of atoms may include heteroatoms such as nitrogen, sulfur, silicon, selenium and oxygen in the backbone or may be composed exclusively of carbon and hydrogen. Aliphatic groups may be substituted or unsubstituted. Exemplary aliphatic groups include, but are not limited to, methyl, ethyl, isopropyl, isobutyl, hydroxymethyl (—$CH_2OH$), mercaptomethyl (—$CH_2SH$), methoxy, methoxycarbonyl ($CH_3OCO$—), nitromethyl (—$CH_2NO_2$), and thiocarbonyl.

The term "alkyl" refers to a linear or branched array of atoms that is composed exclusively of carbon and hydrogen. The array of atoms may include single bonds, double bonds, or triple bonds (typically referred to as alkane, alkene, or alkyne). Alkyl groups may be substituted (i.e. one or more hydrogen atoms is replaced) or unsubstituted. Exemplary alkyl groups include, but are not limited to, methyl, ethyl, and isopropyl. It should be noted that alkyl is a subset of aliphatic.

The term "aromatic" refers to an array of atoms having a valence of at least one and comprising at least one aromatic group. The array of atoms may include heteroatoms such as nitrogen, sulfur, selenium, silicon and oxygen, or may be composed exclusively of carbon and hydrogen. Aromatic groups may be substituted or unsubstituted. Exemplary aromatic groups include, but are not limited to, phenyl, pyridyl, furanyl, thienyl, naphthyl and biphenyl.

The term "aryl" refers to an aromatic radical composed entirely of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms). It should be noted that aryl is a subset of aromatic.

The term "cycloaliphatic" refers to an array of atoms which is cyclic but which is not aromatic. The cycloaliphatic group may include heteroatoms such as nitrogen, sulfur, selenium, silicon and oxygen in the ring, or may be composed exclusively of carbon and hydrogen. A cycloaliphatic group may comprise one or more noncyclic components. For example, a cyclohexylmethyl group ($C_6H_{11}CH_2$—) is a cycloaliphatic functionality, which comprises a cyclohexyl ring (the array of atoms which is cyclic but which is not aromatic) and a methylene group (the noncyclic component). Cycloaliphatic groups may be substituted or unsubstituted. Exemplary cycloaliphatic groups include, but are not limited to, cyclopropyl, cyclobutyl, 1,1,4,4-tetramethylcyclobutyl, piperidinyl, and 2,2,6,6-tetramethylpiperydinyl.

The term "cycloalkyl" refers to an array of atoms which is cyclic but is not aromatic, and which is composed exclusively of carbon and hydrogen. Cycloalkyl groups may be substituted or unsubstituted. It should be noted that cycloalkyl is a subset of cycloaliphatic.

In the definitions above, the term "substituted" refers to at least one hydrogen atom on the named radical being substituted with another functional group, such as alkyl, halogen, —OH, —CN, —NO$_2$, —COOH, etc.

Unless specified otherwise, all test standards refer to the most current standard available as of the filing date of this application.

The term "phr" stands for parts per hundred rubber, and is understood by those of ordinary skill in the art to refer to the amount of a non-rubbery additive per one hundred parts of elastomer. The term "pbw" stands for parts by weight, and is understood to refer to the amount of an ingredient to be added to a composition, and is different from the weight percentage of the ingredient in the composition. The total pbw of all ingredients in the composition can add up to more than 100 parts, while the total weight percentage of all ingredients in the composition is always 100%.

The term "copolymer" refers to a polymer which is derived from two or more monomers (endcaps excluded). The term "dipolymer" refers to a polymer which is derived from only two monomers (endcaps excluded).

Increasing demand for smaller, light-weight and high performance parts have led to advances in process and part design. Thin-wall molding is one such processing capability that uses higher pressures, higher injection speeds, and faster cooling times for molding complex and intricate parts. Standard polymers with too low a flow rate are unable to fill the mold in a timely manner, limiting throughput. Polymers with too high a flow rate are too brittle for practical molding, and shatter on ejecting from the mold or break during use.

The present disclosure generally relates to high flow ductile polycarbonate copolymer compositions which exhibit a balance of favorable flow properties, good aesthetics, biocompatibility, and good physical properties. These copolymer compositions offer superior processing and longer flow length compared to standard polycarbonates, which permits them to be used for molding thin walls. These compositions also have better mold release, lower part-to-part friction, and equal or better gamma color stability compared to standard polycarbonates. They can be considered "green" products since one of the monomers can be derived from natural products (i.e. castor bean oil). The polycarbonate compositions comprise (A) at least one poly (aliphatic ester)-polycarbonate copolymer, (B) a mold release agent, and (C) a radiation stabilizer.

As used herein, the terms "polycarbonate" and "polycarbonate polymer" mean compositions having repeating structural carbonate units of the formula (1):

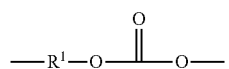

(1)

in which at least about 60 percent of the total number of $R^1$ groups are aromatic organic radicals and the balance thereof are aliphatic, alicyclic, or aromatic radicals. An ester unit (—COO—) is not considered a carbonate unit, and a carbonate unit is not considered an ester unit. In one embodiment, each $R^1$ is an aromatic organic radical, for example a radical of the formula (2):

(2)

wherein each of $A^1$ and $A^2$ is a monocyclic divalent aryl radical and $Y^1$ is a bridging radical having one or two atoms that separate $A^1$ from $A^2$. In an exemplary embodiment, one atom separates $A^1$ from $A^2$. Illustrative non-limiting examples of radicals of this type are —O—, —S—, —S(O)—, —S(O$_2$)—, —C(O)—, methylene, cyclohexyl-methylene, 2-[2.2.1]-bicycloheptylidene, ethylidene, isopropylidene, neopentylidene, cyclohexylidene, cyclopentadecylidene, cyclododecylidene, and adamantylidene. The bridging radical $Y^1$ may be a hydrocarbon group or a saturated hydrocarbon group such as methylene, cyclohexylidene, or isopropylidene.

Polycarbonates may be produced by the interfacial reaction of dihydroxy compounds having the formula HO—$R^1$—OH, wherein $R^1$ is as defined above. Dihydroxy compounds suitable in an interfacial reaction include the dihydroxy compounds of formula (A) as well as dihydroxy compounds of formula (3)

(3)

wherein $Y^1$, $A^1$ and $A^2$ are as described above. Also included are bisphenol compounds of general formula (4):

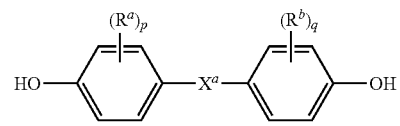

(4)

wherein $R^a$ and $R^b$ each represent a halogen atom or a monovalent hydrocarbon group and may be the same or different; p and q are each independently integers of 0 to 4; and $X^a$ represents one of the groups of formula (5):

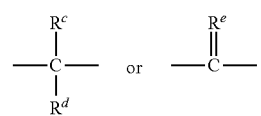

(5)

wherein $R^c$ and $R^d$ each independently represent a hydrogen atom or a monovalent linear or cyclic hydrocarbon group and $R^e$ is a divalent hydrocarbon group.

Specific examples of the types of bisphenol compounds that may be represented by formula (3) include 1,1-bis(4-hydroxyphenyl)methane, 1,1-bis(4-hydroxyphenyl)ethane, 2,2-bis(4-hydroxyphenyl)propane (hereinafter "bisphenol-A" or "BPA"), 2,2-bis(4-hydroxyphenyl)butane, 2,2-bis(4-hydroxyphenyl) octane, 1,1-bis(4-hydroxyphenyl)propane, 1,1-bis(4-hydroxyphenyl)n-butane, 2,2-bis(4-hydroxy-1-methylphenyl)propane, and 1,1-bis(4-hydroxy-t-butylphenyl)propane. Combinations comprising at least one of the foregoing dihydroxy compounds may also be used.

Other useful dihydroxy compounds include aromatic dihydroxy compounds of formula (6):

(6)

wherein each $R^k$ is independently a $C_{1-10}$ hydrocarbon group, and n is 0 to 4. The halogen is usually bromine. Examples of compounds that may be represented by the formula (6) include resorcinol, substituted resorcinol compounds such as 5-methyl resorcinol, 5-phenyl resorcinol, 5-cumyl resorcinol, or the like; catechol; hydroquinone; substituted hydroquinones such as 2-methyl hydroquinone, 2-t-butyl hydroquinone, 2-phenyl hydroquinone, 2-cumyl hydroquinone, 2,3,5,6-tetramethyl hydroquinone, or the like; or combinations comprising at least one of the foregoing compounds.

Polycarbonates may be branched. The branched polycarbonates may be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane (THPE), isatin-bis-phenol, tris-phenol TC (1,3,5-tris((p-hydroxyphenyl)isopropyl)benzene), tris-phenol PA (4(4(1,1-bis(p-hydroxyphenyl)-ethyl) alpha, alpha-dimethyl benzyl)phenol), 4-chloroformyl phthalic anhydride, trimesic acid, and benzophenone tetracarboxylic acid. The branching agents may be added at a level of about 0.05 wt % to about 2.0 wt %.

In specific embodiments, the dihydroxy compound used to form the polycarbonate has the structure of Formula (I):

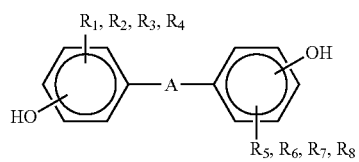

Formula (I)

wherein $R_1$ through $R_8$ are each independently selected from hydrogen, nitro, cyano, $C_1$-$C_{20}$ alkyl, $C_4$-$C_{20}$ cycloalkyl, and $C_6$-$C_{20}$ aryl; and A is selected from a bond, —O—, —S—, —SO$_2$—, $C_1$-$C_{12}$ alkyl, $C_6$-$C_{20}$ aromatic, and $C_6$-$C_{20}$ cycloaliphatic.

In specific embodiments, the dihydroxy compound of Formula (I) is 2,2-bis(4-hydroxyphenyl)propane (i.e. bisphenol-A or BPA). Other illustrative compounds of Formula (I) include: 2,2-bis(4-hydroxy-3-isopropylphenyl)propane; 2,2-bis(3-t-butyl-4-hydroxyphenyl)propane; 2,2-bis(3-phenyl-4-hydroxyphenyl)propane; 1,1-bis(4-hydroxyphenyl) cyclohexane; 4,4'dihydroxy-1,1-biphenyl; 4,4'-dihydroxy-3, 3'-dimethyl-1,1-biphenyl; 4,4'-dihydroxy-3,3'-dioctyl-1,1-biphenyl; 4,4'-dihydroxydiphenylether; 4,4'-dihydroxydiphenylthioether; and 1,3-bis(2-(4-hydroxyphenyl)-2-propyl)benzene.

The polycarbonate compositions of the present disclosure contain at least one poly(aliphatic ester)-polycarbonate copolymer (A). The poly(aliphatic ester)-polycarbonate copolymer is made up of a combination of carbonate units and aliphatic ester units.

In embodiments, the ester unit may have the structure of Formula (II):

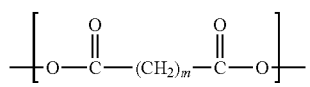

Formula (II)

wherein m is from about 4 to about 18. In some embodiments, m is from about 8 to about 10. The ester units may be derived from a $C_6$-$C_{20}$ aliphatic dicarboxylic acid (which includes the terminal carboxylate groups) or a reactive derivative thereof, including a $C_8$-$C_{12}$ aliphatic dicarboxylic acid. In some embodiments, the terminal carboxylate groups are derived from the corresponding dicarboxylic acid or reactive derivative thereof, such as the acid halide (specifically, the acid chloride), an ester, or the like. Exemplary dicarboxylic acids (from which the corresponding acid chlorides may be derived) include $C_6$ dicarboxylic acids such as hexanedioic acid (also referred to as adipic acid); $C_{10}$ dicarboxylic acids such as decanedioic acid (also referred to as sebacic acid); and alpha, omega $C_{12}$ dicarboxylic acids such as dodecanedioic acid (sometimes abbreviated as DDDA). It will be appreciated that the aliphatic dicarboxylic acid is not limited to these exemplary carbon chain lengths, and that other chain lengths within the $C_6$-$C_{20}$ range may be used.

A specific embodiment of a poly(aliphatic ester)-polycarbonate copolymer/dipolymer having ester units comprising a straight chain methylene group and a polycarbonate group is shown in Formula (III):

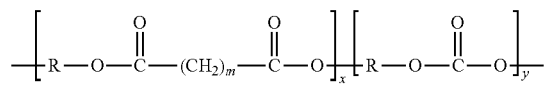

Formula (III)

where m is 4 to 18; x and y represent average molar percentages of the aliphatic ester units and the carbonate units in the copolymer. The average molar percentage ratio x:y may be from 99:1 to 1:99, including from about 13:87 to about 2:98, or from about 9:91 to about 2:98 or from about 8:92 to 13:87. Each R may be independently derived from a dihydroxy compound, such as bisphenol-A. In a specific exemplary embodiment, a useful poly(aliphatic ester)-polycarbonate copolymer/dipolymer comprises sebacic acid ester units and bisphenol A carbonate units (Formula (II), where m is 8, and the average molar ratio of x:y is 6:94). Such poly(aliphatic ester)-polycarbonate copolymers are commercially available as LEXAN HFD copolymers (LEXAN is a trademark of SABIC Innovative Plastics IP B. V.).

In some embodiments, the poly(aliphatic ester)polycarbonate copolymer may have a weight average molecular weight of from about 15,000 to about 40,000, including from about 20,000 to about 38,000 (measured by GPC based on BPA polycarbonate standards). The polycarbonate compositions of the present disclosure may include from about 30 wt % to about 85 wt % of the poly(aliphatic ester)-polycarbonate copolymer.

In some embodiments of the present disclosure, the polycarbonate composition includes two poly(aliphatic ester)-polycarbonate copolymers, i.e. a first poly(aliphatic ester)-polycarbonate copolymer (A1) and a second poly(aliphatic ester)-polycarbonate copolymer (A2). The two poly(aliphatic ester)-polycarbonate copolymers may have the same or different ester unit and the same or different carbonate unit.

The second poly(aliphatic ester)-polycarbonate copolymer has a greater weight average molecular weight than the first poly(aliphatic ester)-polycarbonate copolymer. The first poly(aliphatic ester)-polycarbonate copolymer may have a weight average molecular weight of from about 15,000 to about 25,000, including from about 20,000 to about 22,000 (measured by GPC based on BPA polycarbonate standards). Referring to Formula (III), the first poly(aliphatic ester)-polycarbonate copolymer may have an average molar percentage ratio x:y of from about 4:96 to about 7:93. The second poly(aliphatic ester)-polycarbonate copolymer may have a weight average molecular weight of 30,000 to about 40,000, including from about 35,000 to about 38,000 (measured by GPC based on BPA polycarbonate standards). Referring to Formula (III), the second poly(aliphatic ester)-polycarbonate copolymer may have an average molar percentage ratio x:y of from about 7:93 to about 13:87. In embodiments, the weight ratio of the first poly(aliphatic ester)-polycarbonate copolymer to the second poly(aliphatic ester)-polycarbonate copolymer may be at least 1:1, and in further embodiments is at least 2:1, at least 3:1, or at least 4:1. In some embodiments, the weight ratio is from about 3:2 to about 20:1 (i.e. from about 1.5 to about 20). Note the weight ratio described here is the ratio of the amounts of the two copolymers in the composition, not the ratio of the molecular weights of the two copolymers. The weight ratio between the two poly(aliphatic ester)-polycarbonate copolymers will affect the flow properties, ductility, and surface aesthetics of the final composition. The composition may contain from about 60 to about 99 wt % of the first poly(aliphatic ester)-polycarbonate copolymer. The composition may contain from about 1 to about 40 wt % of the second poly(aliphatic ester)-polycarbonate copolymer. In specific embodiments, the composition contains from about 70 to about 99 wt % of the first poly(aliphatic ester)-polycarbonate copolymer and from about 3 to about 30 wt % of the second poly(aliphatic ester)-polycarbonate copolymer.

In particular embodiments, the poly(aliphatic ester)-polycarbonate copolymer may have from 4.0 mole % to 12.0 mole % of sebacic acid (of the copolymer). In more specific embodiments, the poly(aliphatic ester)-polycarbonate copolymer may have about 6.0 mole % or about 8.25 mole % of sebacic acid.

In particular embodiments, the poly(aliphatic ester)-polycarbonate copolymer may have a biocontent of from about 4 wt % to about 10 wt %. The biocontent can be measured according to ASTM D6866.

The poly(aliphatic ester)-polycarbonate copolymer (A) can be manufactured by processes known in the art, such as interfacial polymerization and melt polymerization. Although the reaction conditions for interfacial polymerization may vary, an exemplary process generally involves dissolving or dispersing a dihydric phenol reactant in aqueous caustic soda or potash, adding the resulting mixture to a suitable water-immiscible solvent medium, and contacting the reactants with a carbonate precursor in the presence of a suitable catalyst such as triethylamine or a phase transfer catalyst, under controlled pH conditions, e.g., about 8 to about 10. Generally, in the melt polymerization process, polycarbonates may be prepared by co-reacting, in a molten state, the dihydroxy reactant(s) and a diaryl carbonate ester, such as diphenyl carbonate, in the presence of a transesterification catalyst in a Banbury™ mixer, twin screw extruder, or the like to form a uniform dispersion. Volatile monohydric phenol is removed from the molten reactants by distillation and the polymer is isolated as a molten residue.

Generally, the poly(aliphatic ester)-polycarbonate copolymer (A) can be made as follows. Bisphenol-A and sebacic acid are weighed, then transferred to a formulation tank which contains methylene chloride, water, triethyamine (catalyst) and a small amount of aqueous sodium hydroxide. The mixture is agitated for 5 minutes and then transferred to the polymerization reactor. Phosgene is added to the reaction mixture over the course of 25 minutes. P-cumylphenol is added to the polymerization reactor over the course of five minutes during the phosgenation. Aqueous sodium hydroxide is additionally added in order to control reaction pH.

Alternatively, sebacic acid is dissolved in a mixture of water and aqueous sodium hydroxide. Bisphenol-A is weighed, then transferred to a formulation tank which contains methylene chloride, water and triethylamine (catalyst). The formulation mixture is transferred to the polymerization reactor. The sebacic acid solution is transferred to the polymerization reactor. Phosgene is added to the reaction mixture over the course of 25 minutes. P-cumylphenol is added to the reactor over the course of five minutes during the phosgenation. Aqueous sodium hydroxide is additionally added in order to control reaction pH.

After completion of the polymerization, the reaction mixture is discharged to the centrifuge feed tank. The polymer solution is purified by feeding the reaction product to a train of liquid/liquid centrifuges. The first centrifuge stage separates the reaction by product brine from the resin solution. The second centrifuge stage removes catalyst from the resin solution by washing with dilute aqueous hydrochloric acid. The third centrifuge stage removes residual ionic species by washing the resin solution with water.

The purified resin solution is then concentrated by evaporation of methylene chloride. The resin is then precipitated by co-feeding the resin solution to a jet with steam to flash off the methylene chloride. Residual methylene chloride is removed from the resin by counter current contact with steam. Excess water is removed from the resin using heated air in a fluidizing dryer.

The thermoplastic compositions of the present disclosure also contain a mold release agent (B). The mold release agent should be biocompatible. Exemplary mold release agents include phthalic acid esters such as dioctyl-4,5-epoxy-hexahydrophthalate; tris-(octoxycarbonylethyl)isocyanurate; tristearin; di- or polyfunctional aromatic phosphates such as resorcinol tetraphenyl diphosphate (RDP), the bis(diphenyl)phosphate of hydroquinone and the bis(diphenyl)phosphate of bisphenol-A; poly-alpha-olefins; epoxidized soybean oil; silicones, including silicone oils; esters, for example, fatty acid esters such as alkyl stearyl esters, e.g., methyl stearate, stearyl stearate, pentaerythritol tetrastearate (PETS), and the like; combinations of methyl stearate and hydrophilic and hydrophobic nonionic surfactants comprising polyethylene glycol polymers, polypropylene glycol polymers, poly(ethylene glycol-co-propylene glycol) copolymers, or a combination comprising at least one of the foregoing glycol polymers, e.g., methyl stearate and polyethylene-polypropylene glycol copolymer in a suitable solvent; waxes such as beeswax, montan wax, paraffin wax, or the like. In particular embodiments, the mold release agent is a poly-alpha-olefin (PAO), or is a vegetable grade pentaerythritol stearate (PETS). Such materials are generally used in amounts of about 0.1 to about 1.0 phr.

The thermoplastic compositions of the present disclosure also contain a gamma-radiation stabilizer (C). Exemplary gamma-radiation stabilizers include alkylene polyols such as ethylene glycol, propylene glycol, 1,3-propanediol, 1,2-butanediol, 1,4-butanediol, meso-2,3-butanediol, 1,2-pentanediol, 2,3-pentanediol, 1,4-pentanediol, 1,4-hexandiol, and the like; cycloalkylene polyols such as 1,2-cyclopentanediol, 1,2-cyclohexanediol, and the like; branched alkylenepolyols such as 2,3-dimethyl-2,3-butanediol (pinacol), and the like, as well as alkoxy-substituted cyclic or acyclic alkanes. Unsaturated alkenols are also useful, examples of which include 4-methyl-4-penten-2-ol, 3-methyl-pentene-3-ol, 2-methyl-4-penten-2-ol, 2,4-dimethyl-4-pene-2-ol, and 9 to decen-1-ol, as well as tertiary alcohols that have at least one hydroxy substituted tertiary carbon, for example 2-methyl-2,4-pentanediol (hexylene glycol), 2-phenyl-2-butanol, 3-hydroxy-3-methyl-2-butanone, 2-phenyl-2-butanol, and the like, and cyclic tertiary alcohols such as 1-hydroxy-1-methyl-cyclohexane. Certain hydroxymethyl aromatic compounds that have hydroxy substitution on a saturated carbon attached to an unsaturated carbon in an aromatic ring can also be used. The hydroxy-substituted saturated carbon can be a methylol group ($-CH_2OH$) or it can be a member of a more complex hydrocarbon group such as $-CR^4HOH$ or $-CR^4OH$ wherein $R^4$ is a complex or a simple hydrocarbon. Specific hydroxy methyl aromatic compounds include benzhydrol, 1,3-benzenedimethanol, benzyl alcohol, 4-benzyloxy benzyl alcohol and benzyl benzyl alcohol. 2-Methyl-2,4-pentanediol (hexylene glycol), polyethylene glycol, and polypropylene glycol are often used for gamma-radiation stabilization. In particular embodiments, hexylene glycol is used. The gamma-radiation stabilizer is present in amounts of about 0.05 to about 1.0 phr.

In further embodiments, the thermoplastic composition also includes an epoxy resin (D). The epoxy resin acts generally as a hydrolytic stabilizer to improve the hydrolytic stability of the overall composition. This can be useful for articles that are sensitive to hydrothermal degradation due to a relatively large and exposed surface area. The epoxy resin may be multifunctional, i.e. contain one or more expoxy groups. The epoxy resin can also contain aromatic and/or aliphatic residues, as well as non-epoxy functional groups. The epoxy resin may be polymeric or non-polymeric. The epoxy resin is present in amounts of about 0.05 to about 1.0 phr.

In some embodiments, the epoxy resin is a polymer with a weight average molecular weight (Mw) of about 1,000 to about 18,000. Exemplary polymers (which as used herein includes oligomers) having multiple epoxy groups include the reaction products of an epoxy-containing ethylenically unsaturated monomer (e.g., a glycidyl($C_{1-4}$alkyl)(meth)acrylate, allyl glycidyl ethacrylate, and glycidyl itoconate) with one or more non-epoxy functional ethylenically unsaturated compounds (e.g., styrene, ethylene, methyl(meth)acrylate, n-butyl acrylate, and the like). Specifically, the epoxy polymer may be the reaction product of an epoxy-functional (meth)acrylate monomer with a non-epoxy functional styrenic and/or ($C_{1-8}$ hydrocarbyl)(meth)acrylate and/or olefin monomer.

The epoxy polymer may be a copolymeric reaction product of a glycidyl(meth)acrylate monomer, ethylene, and optionally a $C_{1-4}$(alkyl)(meth)acrylate monomer. Useful commercially available terpolymers of this type include the ethylene-methyl acrylate-glycidyl methacrylate terpolymers sold under the trade name LOTADER by Atofina.

The epoxy polymer may be the reaction product of an epoxy-functional (meth)acrylate monomer, a non-epoxy functional styrenic monomer, and optionally a non-epoxy functional $C_{1-8}$(hydrocarbyl)(meth)acrylate monomer.

Other epoxy resins are commercially available from Johnson Polymer, LLC (now BASF). Epoxy-functional styrene-(meth)acrylate copolymers with glycidyl groups are commercially available from Johnson Polymer, LLC (now BASF) under the Joncryl™ trade name, for example the Joncryl ADR-4368CS material. The epoxy resin may be Joncryl ADR-4368CS. Other epoxy compounds are available from Dow Chemical Company under the trade names DER 332, DER 661, and DER 667, or from Hexion under the trade names EPON 826, EPON 828, EPON 1001F, EPON 1004F, EPON 1005F, EPON 1007F, and EPON 1009F, or from Ciba Products under the trade name Araldite CY 182, or from Dow under the trade names ERL-4221 and ERL-4299, and the like. 3,4-epoxycyclohexyl-3,4 epoxycyclohexylcarboxylate is commercially available from Union Carbide Corporation.

Other additives ordinarily incorporated in polycarbonate compositions of this type can also be used, with the proviso that the additives are selected so as to not significantly adversely affect the desired properties of the polycarbonate. Combinations of additives can be used. Such additives can be mixed at a suitable time during the mixing of the components for forming the composition. In embodiments, one or more additives are selected from at least one of the following: antioxidants, colorants, and flame retardants.

Exemplary antioxidant additives include, for example, organophosphites such as tris(nonyl phenyl)phosphite, tris (2,4-di-t-butylphenyl)phosphite (e.g., "IRGAPHOS 168" or "I-168"), bis(2,4-di-t-butylphenyl)pentaerythritol diphosphite, distearyl pentaerythritol diphosphite or the like; alkylated monophenols or polyphenols; alkylated reaction products of polyphenols with dienes, such as tetrakis[methylene (3,5-di-tert-butyl-4-hydroxyhydrocinnamate)]methane, or the like; butylated reaction products of para-cresol or dicyclopentadiene; alkylated hydroquinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds such as distearylthiopropionate, dilaurylthiopropionate, ditridecylthiodipropionate, octadecyl-3-(3,5-di-tert-butyl-4-hydroxyphenyl)propionate, pentaerythrityl-tetrakis[3-(3,5-di-tert-butyl-4-hydroxyphenyl)propionate or the like; amides of beta-(3,5-di-tert-butyl-4-hydroxyphenyl)-propionic acid or the like, or combinations comprising at least one of the foregoing antioxidants. Antioxidants are generally used in amounts of about 0.01 to about 1.0 phr.

Exemplary heat stabilizer additives include, for example, organophosphites such as triphenyl phosphite, tris-(2,6-dimethylphenyl)phosphite, tris-(mixed mono- and di-nonylphenyl)phosphite or the like; phosphonates such as dimethylbenzene phosphonate or the like, phosphates such as trimethyl phosphate, or the like, or combinations comprising at least one of the foregoing heat stabilizers. Heat stabilizers are generally used in amounts of about 0.01 to about 1.0 phr.

Light stabilizers and/or ultraviolet light (UV) absorbing additives can also be used. Exemplary light stabilizer additives include, for example, benzotriazoles such as 2-(2-hydroxy-5-methylphenyl)benzotriazole, 2-(2-hydroxy-5-tert-octylphenyl)-benzotriazole and 2-hydroxy-4-n-octoxy benzophenone, or the like, or combinations comprising at least one of the foregoing light stabilizers. Light stabilizers are generally used in amounts of about 0.01 to about 1.0 phr.

Exemplary UV absorbing additives include for example, hydroxybenzophenones; hydroxybenzotriazoles; hydroxybenzotriazines; cyanoacrylates; oxanilides; benzoxazinones; 2-(2H-benzotriazol-2-yl)-4-(1,1,3,3-tetramethylbutyl)-phenol (CYASORB™ 5411); 2-hydroxy-4-n-octyloxybenzophenone (CYASORB™ 531); 2[4,6-bis(2,4-dimethylphenyl)-1,3,5-triazin-2-yl]-5-(octyloxy)-phenol (CYASORB™ 1164); 2,2'-(1,4-phenylene)bis(4H-3,1-benzoxazin-4-one) (CYASORB™ UV-3638); 1,3-bis[(2-cyano-3,3-diphenylacryloyl)oxy]-2,2-bis[[(2-cyano-3,3-diphenylacryloyl)oxy] methyl]propane (UVINUL™ 3030); 2,2'-(1,4-phenylene)bis (4H-3,1-benzoxazin-4-one); 1,3-bis[(2-cyano-3,3-diphenylacryloyl)oxy]-2,2-bis[[(2-cyano-3,3-diphenylacryloyl)oxy]methyl]propane; nano-size inorganic materials such as titanium oxide, cerium oxide, and zinc oxide, all with particle size less than or equal to 100 nanometers; or the like, or combinations comprising at least one of the foregoing UV absorbers. UV absorbers are generally used in amounts of about 0.01 to about 1.0 phr.

Colorants such as pigment and/or dye additives can also be present in order to offset any color that may be present in the polycarbonate resin and to provide desired color to the customer. Useful pigments can include, for example, inorganic pigments such as metal oxides and mixed metal oxides such as zinc oxide, iron oxides, or the like; sulfides such as zinc sulfides, or the like; aluminates; sodium sulfo-silicates sulfates, chromates, or the like; carbon blacks; zinc ferrites; ultramarine blue; organic pigments such as azos, di-azos, quinacridones, perylenes, naphthalene tetracarboxylic acids, flavanthrones, isoindolinones, tetrachloroisoindolinones, anthraquinones, enthrones, dioxazines, phthalocyanines, and azo lakes; Pigment Red 101, Pigment Red 122, Pigment Red 149, Pigment Red 177, Pigment Red 179, Pigment Red 202, Pigment Violet 29, Pigment Blue 15, Pigment Blue 60, Pigment Green 7, Pigment Yellow 119, Pigment Yellow 147, Pigment Yellow 150, and Pigment Brown 24; or combinations comprising at least one of the foregoing pigments. Pigments are generally used in amounts of about 0.00001 to about 10.0 phr.

Exemplary dyes are generally organic materials and include, for example, coumarin dyes such as coumarin 460 (blue), coumarin 6 (green), nile red or the like; lanthanide complexes; hydrocarbon and substituted hydrocarbon dyes; polycyclic aromatic hydrocarbon dyes; scintillation dyes such as oxazole or oxadiazole dyes; aryl- or heteroaryl-substituted poly (C2-8) olefin dyes; carbocyanine dyes; indanthrone dyes; phthalocyanine dyes; oxazine dyes; carbostyryl dyes; napthalenetetracarboxylic acid dyes; porphyrin dyes; bis(styryl)biphenyl dyes; acridine dyes; anthraquinone dyes; cyanine dyes; methine dyes; arylmethane dyes; azo dyes; indigoid dyes, thioindigoid dyes, diazonium dyes; nitro dyes; quinone imine dyes; aminoketone dyes; tetrazolium dyes; thiazole dyes; perylene dyes, perinone dyes; bis-benzoxazolylthiophene (BBOT); triarylmethane dyes; xanthene dyes; thioxanthene dyes; naphthalimide dyes; lactone dyes; fluorophores such as anti-stokes shift dyes which absorb in the near infrared wavelength and emit in the visible wavelength, or the like; luminescent dyes such as 7-amino-4-methylcoumarin; 3-(2'-benzothiazolyl)-7-diethylaminocoumarin; 2-(4-biphenylyl)-5-(4-t-butylphenyl)-1,3,4-oxadiazole; 2,5-bis-(4-biphenylyl)-oxazole; 2,2'-dimethyl-p-quaterphenyl; 2,2-dimethyl-p-terphenyl; 3,5,3'''',5''''-tetra-t-butyl-p-quinquephenyl; 2,5-diphenylfuran; 2,5-diphenyloxazole; 4,4'-diphenylstilbene; 4-dicyanomethylene-2-methyl-6-(p-dimethylaminostyryl)-4H-pyran; 1,1'-diethyl-2,2'-carbocyanine iodide; 3,3'-diethyl-4,4',5,5'-dibenzothiatricarbocyanine iodide; 7-dimethylamino-1-methyl-4-methoxy-8-azaquinolone-2; 7-dimethylamino-4-methylquinolone-2; 2-(4-(4-dimethylaminophenyl)-1,3-butadienyl)-3-ethylbenzothiazolium perchlorate; 3-diethylamino-7-diethyliminophenoxazonium perchlorate; 2-(1-naphthyl)-5-phenyloxazole; 2,2'-p-phenylen-bis(5-phenyloxazole); rhodamine 700; rhodamine 800; pyrene, chrysene, rubrene, coronene, or the like; or combinations comprising at least one of the foregoing dyes. Dyes are generally used in amounts of about 0.00001 to about 10.0 phr.

The polycarbonate composition may further comprise one or more flame retardant additives. Desirably, the flame retardant additive does not contain bromine or chlorine. The flame retardant additive may be a perfluoroalkane sulfonate, such as potassium perfluorobutane sulfonate ("Rimar salt"). Another example of a flame retardant additive is potassium diphenylsulfon-3-sulfonate ("KSS") or sodium toluene sulfonate (NaTS). Alternatively, the flame retardant additive may be a phosphorous-containing flame retardant compound, such as an organic phosphate or an organic compound containing phosphorus-nitrogen bonds. One type of exemplary organic phosphate is an aromatic phosphate of the formula $(GO)_3P=O$, wherein each G is independently an alkyl, cycloalkyl, aryl, alkaryl, or aralkyl group, provided that at least one G is an aromatic group. Two of the G groups may be joined together to provide a cyclic group, for example, diphenyl pentaerythritol diphosphate. A specific aromatic phosphate is one in which each G is aromatic, for example, triphenyl phosphate, tricresyl phosphate, isopropylated triphenyl phosphate, and the like. Di- or polyfunctional aromatic phosphorus-containing compounds are also useful, for example, compounds of the formulas (II-a), (II-b), and (II-c) below:

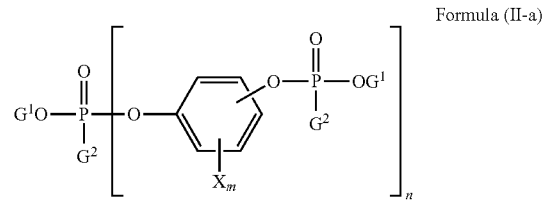

Formula (II-a)

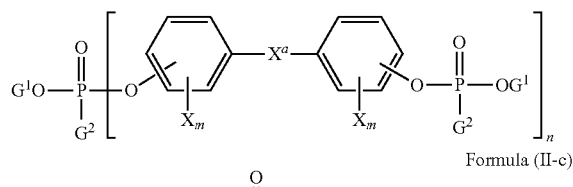

Formula (II-b)

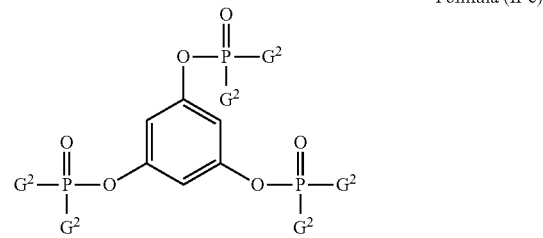

Formula (II-c)

wherein each $G^1$ is independently a hydrocarbon having 1 to about 30 carbon atoms; each $G^2$ is independently a hydrocarbon or hydrocarbonoxy having 1 to about 30 carbon atoms; each X is independently a bromine or chlorine; m 0 to 4, and n is 1 to about 30. Examples of suitable di- or polyfunctional aromatic phosphorus-containing compounds include resorcinol tetraphenyl diphosphate (RDP), the bis (diphenyl)phosphate of hydroquinone and the bis(diphenyl) phosphate of bisphenol-A, and the like. The flame retardant additive is generally used in amounts of about 0.001 to about 5.0 phr.

In additional embodiments, the polycarbonate composition comprises a poly(aliphatic ester)-polycarbonate copolymer (A1) having a Mw of from about 15,000 to about 25,000; a poly(aliphatic ester)-polycarbonate copolymer (A2) having a Mw of from about 30,000 to about 40,000; a mold release agent (B); and a radiation stabilizer (C), wherein the weight ratio of copolymer (A1) to copolymer (A2) is from about 3:2 to about 20:1, or from about 3:1 to about 19:1. The mold release agent (B) is present in an amount of about 0.1 to about 1.0 phr. The radiation stabilizer (C) is present in an amount of about 0.05 to about 1.0 phr. An epoxy resin (D) can also be present in an amount of about 0.05 to about 1.0 phr.

The polycarbonate compositions of the present disclosure have a combination of good impact strength, good flow properties, good thermal properties, and good optical properties.

The polycarbonate compositions of the present disclosure generally have a melt flow rate (MFR) of about 25 (grams per 10 minutes) g/10 min or higher, when measured at 300° C., 1.2 kg load according to ASTM D1238. In other embodiments, the polycarbonate compositions have a MFR of about 40 g/10 min or higher, or about 55 g/10 min or higher, or about 100 g/10 min or higher, or from about 25 g/10 min to about 55 g/10 min. The polycarbonate compositions may have a maximum MFR of about 125 g/10 min.

The polycarbonate compositions of the present disclosure also have a light transmittance (% LT) of 80% or higher, when measured at 2.54 mm thickness according to ASTM D1003. The polycarbonate compositions of the present disclosure also have a haze of 1% or less, when measured at 2.54 mm thickness according to ASTM D1003.

The polycarbonate compositions of the present disclosure can have a heat distortion temperature (HDT) of 120° C. or less when measured at 1.82 MPa, 3.2 mm thickness according to ASTM D648. In other embodiments, the polycarbonates have a HDT of 133° C. or lower, or a HDT of 121° C. or higher, or of 134° C. or higher. In this regard, autoclaving is a method used to sterilize equipment and supplies, and is commonly used in medical settings. The equipment/supplies are subjected to high pressure saturated steam having a temperature of 121° C. or 134° C. It is contemplated that the polycarbonate compositions can be tuned to either be autoclavable or to be distorted/warped when autoclaved. This ability is useful, for example if it is desired that a particular article be distorted under autoclaving conditions to ensure the article is single-use only and cannot be reused.

The polycarbonate compositions of the present disclosure may have a notched Izod impact strength (INI) of 680 J/m or higher, when measured at 23° C. according to ASTM D256. In more specific embodiments, the polycarbonate compositions have an INI of 750 J/m or higher when measured at 23° C.

The polycarbonate compositions of the present disclosure may have a notched Izod impact strength (INI) of 450 J/m or higher, when measured at 0° C. according to ASTM D256. In more specific embodiments, the polycarbonate compositions have an INI of 750 J/m or higher when measured at 0° C.

The polycarbonate compositions of the present disclosure may have a tensile modulus of 2300 MPa or higher, when measured at 50 mm/min according to ASTM D638.

The polycarbonate compositions of the present disclosure may have a peak instrumented impact energy of 60 J or higher, when measured at 23° C. according to ASTM D3763.

The polycarbonate compositions of the present disclosure may have any combination of these properties (MFR, % LT/haze, HDT, INI, tensile modulus, impact energy), and any combination of the listed values for these properties. It should be noted that some of the properties (e.g. INI) are measured using articles made from the polycarbonate composition; however, such properties are described as belonging to the polycarbonate composition for ease of reference.

In some embodiments, the polycarbonate compositions have an MFR of about 25 g/10 min or higher; a light transmittance (% LT) of 80% or higher and a haze of 1% or less when measured at 2.54 mm thickness; and a heat distortion temperature (HDT) of 120° C. or less when measured at 1.82 MPa, 3.2 mm thickness.

In other embodiments, the polycarbonate compositions have an MFR of about 40 g/10 min or higher; a light transmittance (% LT) of 80% or higher and a haze of 1% or less when measured at 2.54 mm thickness; and a heat distortion temperature (HDT) of 120° C. or less when measured at 1.82 MPa, 3.2 mm thickness.

In other embodiments, the polycarbonate compositions have an MFR of about 40 g/10 min or higher; a light transmittance (% LT) of 80% or higher and a haze of 1% or less when measured at 2.54 mm thickness; a notched Izod impact strength (INI) of 680 J/m or higher, when measured at 23° C.; a notched Izod impact strength (INI) of 450 J/m or higher, when measured at 0° C.; and a peak instrumented impact energy of 60 J or higher, when measured at 23° C.

The polycarbonate compositions of the present disclosure are also biocompatible. Biocompatibility can be determined according to ISO 10993. In this regard, some exemplary polycarbonate compositions have passed the L929 Neutral Red uptake cytotoxicity test (10993-5), the Kligman maximization test (10993-10), the intracutaneous injection test (10993-10), the systemic injection test (10993-11), the rabbit pyrogen test (10993-11), and intramuscular implantation test (10993-6). Exemplary compositions have also passed the hemolytic blood test (ASTM F756-08), the USP Physicochemical Test for Plastics (USP 35, <661>), and the USP Physicochemical Test for Non-Volatile Residue (USP 35, <661>).

The polycarbonate compositions of the present disclosure may be molded into pellets. The compositions may be molded, foamed, or extruded into various structures or articles by known methods, such as injection molding, overmolding, extrusion, rotational molding, blow molding and thermoforming.

In particular, it is contemplated that the polycarbonate compositions of the present disclosure are used to mold thin-wall non-implantable articles for medical applications, particularly articles that come into contact with internal bodily fluids (especially blood). Non-limiting examples of such medical articles include blood bowls, disposable hypodermic syringes, needle shields, tubing/lines, connectors, needle wings (i.e. butterfly needle), cannulae, safety barrels, filter media, sharps containers, trays, injectable drug vials, prescription pill vials, inhaler parts, IV drug or saline bags, blood bags, and transfusion/retransfusion bags. Generally, these medical articles do not include electronic components. Other exemplary articles include housings for medical devices, for example dialyzer housings, transfusion systems, etc.

Other exemplary articles that can be used in medical applications may include irrigation solution bottles; fluid replacement bottles; nose spray bottles; packaging blisters; and non-woven textile goods, such as surgical gowns, isolation gowns, isolation drapes, sterilization wraps, and face masks.

Some articles that can be used in a medical/research setting include centrifuge tubes, pipette tips, multi-well plates, diagnostic cuvettes, and urine or other sample cups. It is contemplated that the polycarbonate compositions described herein could be used instead of polypropylene as well.

The present disclosure further contemplates additional fabrication operations on said articles, such as, but not limited to, molding, in-mold decoration, baking in a paint oven, lamination, and/or thermoforming. The polycarbonate compositions are especially useful for making articles that have parts with a wall thickness of 5.0 mm or less, 2.0 mm or less, 0.5 mm or less, or 0.3 mm or less. It is recognized that molded parts can have walls that vary in thickness, and these values of 5.0 mm/2.0 mm/0.5 mm/0.3 mm or less refer to the thinnest parts of those walls, or the "thinnest thickness". Put another way, the article has at least one wall that is 5.0 mm/2.0 mm/0.5 mm/0.3 mm or less in thickness.

The following examples are provided to illustrate the polycarbonate compositions, articles, and methods of the present disclosure. The examples are merely illustrative and are not intended to limit the disclosure to the materials, conditions, or process parameters set forth therein.

EXAMPLES

Table 1 lists the names and descriptions of the ingredients used in the following Examples.

TABLE 1

| Ingredient | Description | Mw | Trade name | Source |
|---|---|---|---|---|
| HFD-low | Sebacic acid-bisphenol A copolymer, 6.0 mol % sebacic acid, PDI = 2.6, biocontent = 5.0%, p-cumylphenol endcap, MFR = 45 g/10 min based on ASTM D1238 | 21,500 | LEXAN | SABIC Innovative Plastics |
| HFD-high | Sebacic acid-bisphenol A copolymer, 8.5 mol % sebacic acid, PDI = 2.7, biocontent = 6.0%, p-cumylphenol endcap, MFR = 6.5 g/10 min based on ASTM D1238 | 36,500 | LEXAN | SABIC Innovative Plastics |
| ADR 4368 | Epoxy resin | | Joncryl | BASF |
| Phosphite | stabilizer | | IRGAPHOS 168 | Ciba |
| PAO | Poly-alpha-olefin, release agent | | | |
| HG | Hexylene glycol, gamma radiation stabilizer | | | |
| PC-1 | Bisphenol A homopolymer, PCP (p-cumylphenol) endcapped | 29,600 | LEXAN | SABIC Innovative Plastics |
| PC-2 | Bisphenol A homopolymer, PCP (p-cumylphenol) endcapped | 21,700 | LEXAN | SABIC Innovative Plastics |
| V-PETS | Vegetable-based Pentaerythritol tetrastearate | | | |

Table 2 lists the ingredients making up three different formulations: HFD-25, HFD-40, and HPS1R. HPS1R is a comparative reference sample to which the other two compositions can be compared, and is based on the use of bisphenol-A homopolymers.

TABLE 2

| Ingredient | Unit | HFD-25 | HFD-40 | HPS1R |
|---|---|---|---|---|
| HFD-low | pbw | 75.0 | 95.0 | — |
| HFD-high | pbw | 25.0 | 5.0 | — |
| PC-1 | pbw | — | — | 90.0 |
| PC-2 | pbw | — | — | 10.0 |
| ADR 4368 | pbw | 0.1 | 0.1 | — |
| Phosphite | pbw | 0.060 | 0.060 | 0.03 |
| PAO | pbw | 0.300 | 0.300 | — |
| V-PETS | pbw | — | — | 0.400 |
| HG | pbw | 0.100 | 0.100 | 0.092 |

All formulations were thoroughly compounded in a 30 mm co-rotating twin screw (Werner & Pfleiderer; ZSK-30) extruder using a melt temperature of 300° C. with a rate of 20 kgs/hr, 20 inches of mercury vacuum and a screw speed of 400 RPM. The extrudate was cooled under water, pelletized and dried at 120° C. for 4 hours with a desiccant bed dryer. To make test specimens, the dried pellets were injection molded using a Van Dorn 80T molding machine at 300° C. melt temperature to form test parts for impact and mechanical testing.

A comparison of physical and mechanical properties is shown in Table 3.

TABLE 3

| | HFD-25 | HFD-40 | HPS1R | Unit | Standard |
|---|---|---|---|---|---|
| Mechanical | | | | | |
| Tensile Stress, brk, 50 mm/min | 61.3 | 51.1 | 65 | MPa | ASTM D638 |
| Tensile Strain, brk, 50 mm/min | 136.28 | 101.92 | 120 | MPa | ASTM D638 |
| Tensile Modulus, 50 mm/min | 2346 | 2350 | 2370 | MPa | ASTM D638 |

TABLE 3-continued

|  | HFD-25 | HFD-40 | HPS1R | Unit | Standard |
|---|---|---|---|---|---|
| Impact |  |  |  |  |  |
| INI, 23° C. | 791 | 693 | 640 | J/m | ASTM D256 |
| INI, 23° C. ductility | 100 | 100 | 100 | % | ASTM D256 |
| INI, 0° C. | 753 | 465 |  |  | ASTM D256 |
| INI, 0° C. ductility | 100 | 20 |  |  | ASTM D256 |
| Instrumented impact Energy @ peak, 23° C. | 62.8 | 62.2 | 54 | J | ASTM D3763 |
| Instrumented impact ductility, 23° C. | 100 | 100 | 100 | % | ASTM D256 |
| Physical |  |  |  |  |  |
| Specific Gravity | 1.2 | 1.2 | 1.2 | — | ASTM D792 |
| Melt Flow Rate, 300° C., 1.2 kgf | 25 | 40 | 25 | g/10 min | ASTM D1238 |
| Thermal |  |  |  |  |  |
| HDT, 0.45 MPa, 3.2 mm, unannealed | 125 | 125 |  | ° C. | ASTM D648 |
| HDT, 1.82 MPa, 3.2 mm, unannealed | 117 | 114 | 126 | ° C. | ASTM D648 |
| Optical |  |  |  |  |  |
| Light Transmission, 3.2 mm thickness | 80 | 80 | 88 | % | ASTM D1003 |
| % Haze, 3.2 mm thickness | <1 | <1 | 1 | % | ASTM D1003 |

It should be noted that the HPS1R resin had a worse INI at 23° C. than the HFD-25 and HFD-40 formulations. The HFD-25 and HFD-40 compositions also had equal or greater MVR with the higher INI value. The impact/flow balance clearly favors the HFD-25 and HFD-40 formulations compared to the HPS1R resin.

In addition, the HFD-25 and HFD-40 formulations were tested for biocompatibility according to ISO 10993 for cytotoxicity, intracutaneous injection (skin irritation), systemic injection, pyrogenicity, hemolysis, physicochemical tests, implantation, and Kligman skin sensitization. Both formulations passed all of the tests.

Sterilization studies were also conducted. Samples of HFD-25, HFD-40, and HPS1R were sterilized by gamma radiation at 25, 50, and 75 kilogray (kGy) dosages. Samples were also sterilized via ethylene oxide (EtO) sterilization. The color shift was measured as delta YI, which is the difference between initial yellowness index prior to sterilization and final yellowness index measured after sterilization. Final yellowness index was measured two weeks after exposure to allow a stable color to be achieved. The Yellowness Index (YI) was measured on 3.2 mm tensile bars before and after sterilization using an X-Rite Color i7 benchtop spectrophotometer in the transmission mode using CIELAB color equation, an observer angle of 2 degrees, and illuminant C as the light source. YI was measured following ASTM E313-73 (D1925).

FIG. 1 is a graph illustrating the delta YI for each composition (HFD-25, HFD-40, and HPS1R) for all four sterilization types on a 3.2 mm thick chip sample (25 kGy on far left, 50 kGy on center left, 75 kGy on center right, and EtO on far right for each composition). The various values are shown in Table 4 below:

TABLE 4

| 3.2 mm chip | 25 kGy | 50 kGy | 75 kGy | EtO |
|---|---|---|---|---|
| HFD-25 | 12.8 | 19.0 | 30.1 | 0.14 |
| HFD-40 | 11.8 | 17.9 | 28.6 | 0.08 |
| HPS1R | 13.7 | 22.3 | 36.1 | 0.96 |

Figure 2:
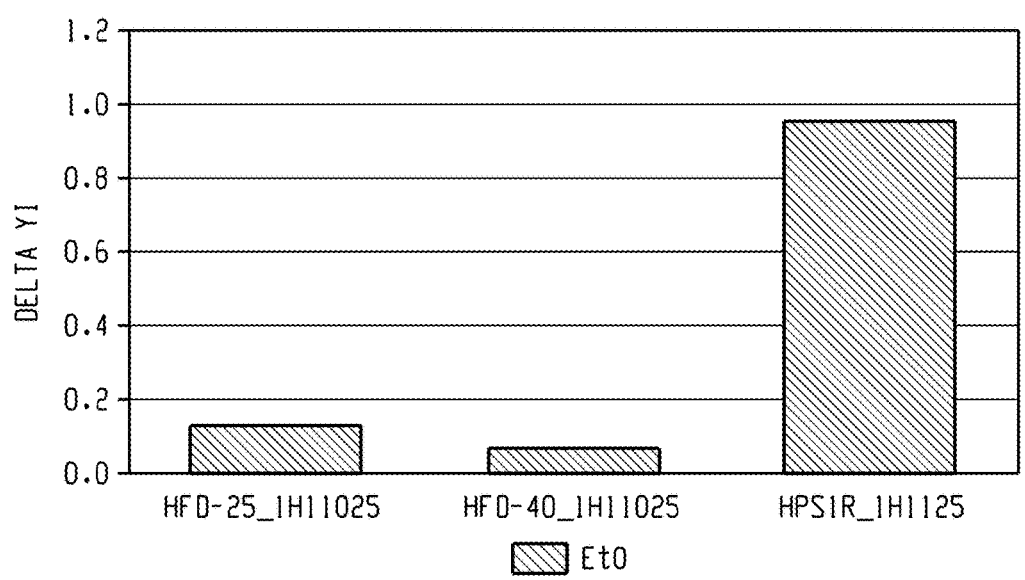
FIG. 2 is a graph illustrating the delta YI for various compositions exposed to ethylene oxide sterilization for chip samples of 3.2 mm thickness. This expands the scale of FIG. 1 to show more detail.

FIG. 2 is a graph illustrating the delta YI for only ethylene oxide sterilization on the 3.2 mm thick chip samples of FIG. 1. Here, the y-axis is magnified to show the differences between the three compositions. Generally, the HFD-25 and HFD-40 samples performed as well as, or better than, the HPS1R comparative sample.

Figure 3:
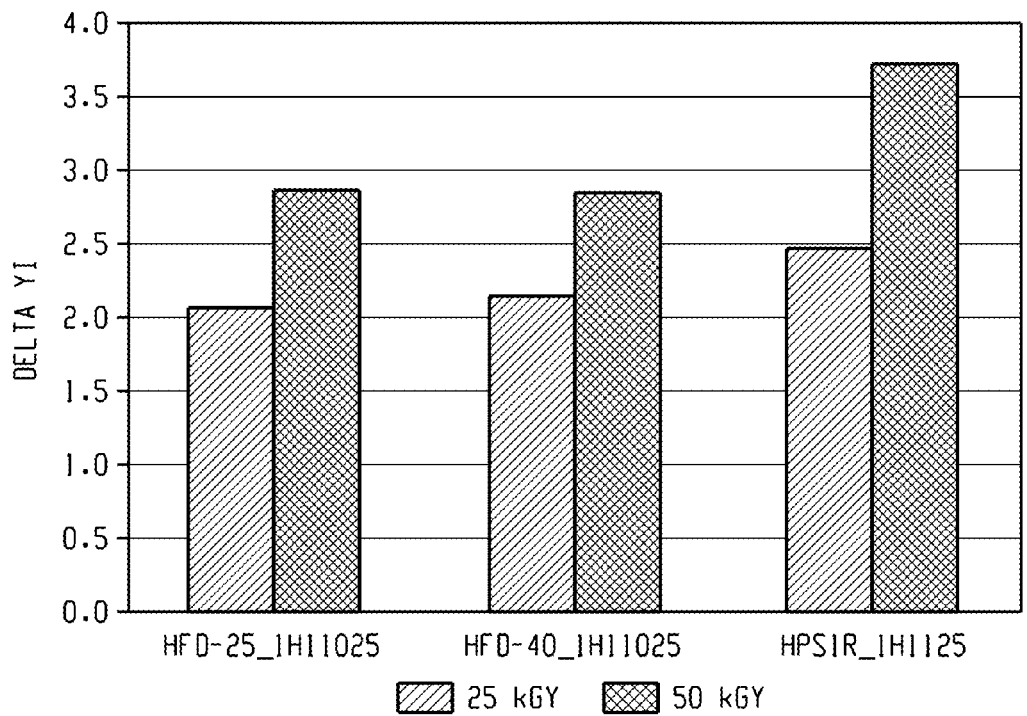
FIG. 3 is a graph illustrating the delta YI for various compositions exposed to different amounts of gamma radiation for chip samples of 0.65 mm thickness.

FIG. 3 is a graph illustrating the delta YI for each composition after 25 kGy (left) and 50 kGy (right) gamma radiation sterilizations on a 0.65 mm thick chip sample. The various values are shown in Table 5 below:

TABLE 5

| 0.65 mm chip | 25 kGy | 50 kGy |
|---|---|---|
| HFD-25 | 2.07 | 2.88 |
| HFD-40 | 2.15 | 2.84 |
| HPS1R | 2.48 | 3.76 |

Again, the HFD-25 and HFD-40 samples performed better than the HPS1R comparative sample. Please note the delta YI was much lower compared to the 3.2 mm samples of FIG. 1.

The HFD-25 and HFD-40 samples exhibited lower yellowness increases compared to the HPS1R sample. In other words, the HFD-25 and HFD-40 samples exhibited improved color shift properties post gamma radiation sterilization and ethylene oxide sterilization.

Mechanical properties were also measured. In particular, multiaxial impact (ASTM D3763), tensile modulus (ASTM D638), elongation at break (ASTM D638), light transmittance (ASTM D1003), and haze (ASTM D1003) were measured before (Control) and after various sterilizations.

Figure 4:
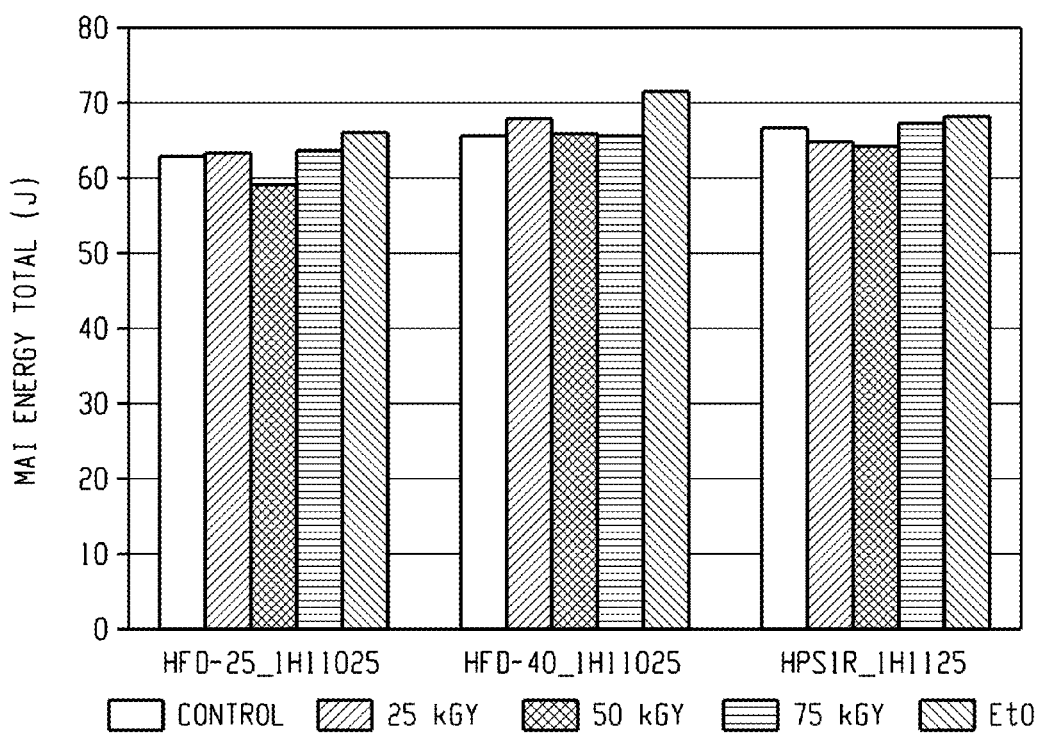
FIG. 4 is a graph illustrating the effect on multiaxial impact strength of various compositions and sterilization treatments for chip samples of 3.2 mm thickness.

FIG. 4 is a graph illustrating multiaxial impact for the various compositions and sterilization types. The control is on the far left, the 25 kGy on the center left, the 50 kGy in the center, the 75 kGy on the center right, and the EtO on the far right for each composition at 3.2 mm thickness. This was measured at 23° C. according to ASTM D3763. The various values are shown in Table 6 below:

TABLE 6

| 3.2 mm chip | Control | 25 kGy | 50 kGy | 75 kGy | EtO |
|---|---|---|---|---|---|
| HFD-25 | 63.3 | 63.8 | 59.5 | 64.1 | 66.2 |
| HFD-40 | 65.9 | 68.2 | 66.2 | 65.9 | 72.3 |
| HPS1R | 66.9 | 65.2 | 64.6 | 67.6 | 68.3 |

Figure 5:
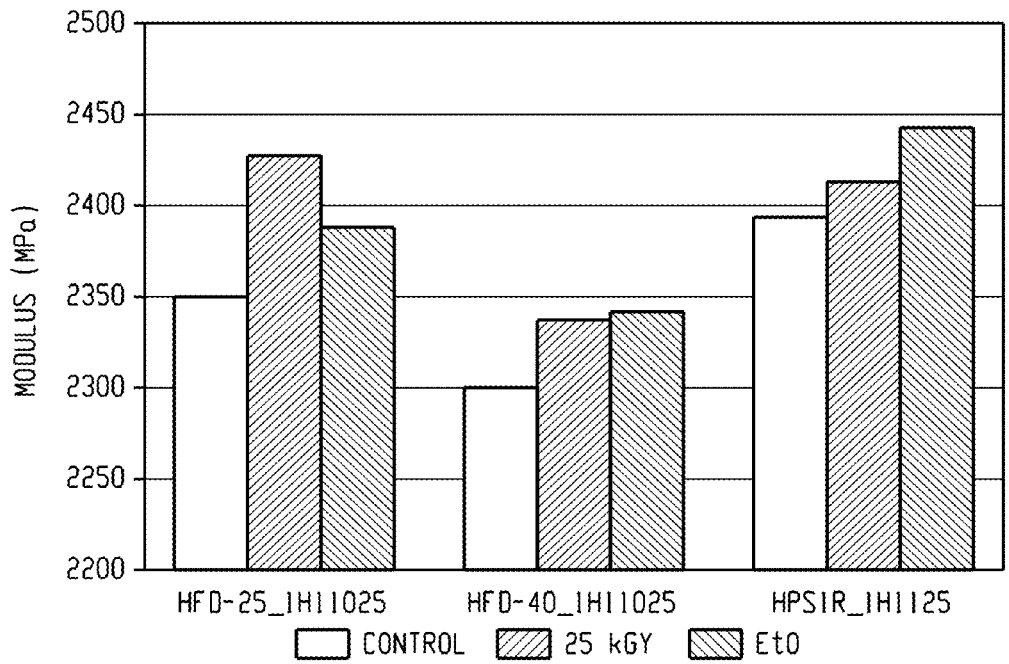
FIG. 5 is a graph illustrating the effect on tensile modulus of various compositions and sterilization treatments for chip samples of 3.2 mm thickness.

FIG. 5 is a graph illustrating tensile modulus for the various compositions after sterilization via 25 kGy gamma radiation and ethylene oxide sterilization at 3.2 mm thickness. The control is on the left, the 25 kGy in the center, and the EtO on the right for each composition. This was measured according to ASTM D638. The various values are shown in Table 7 below:

TABLE 7

| 3.2 mm chip | Control | 25 kGy | EtO |
|---|---|---|---|
| HFD-25 | 2350 | 2428 | 2388 |
| HFD-40 | 2300 | 2338 | 2348 |
| HPS1R | 2394 | 2414 | 2444 |

Figure 6:
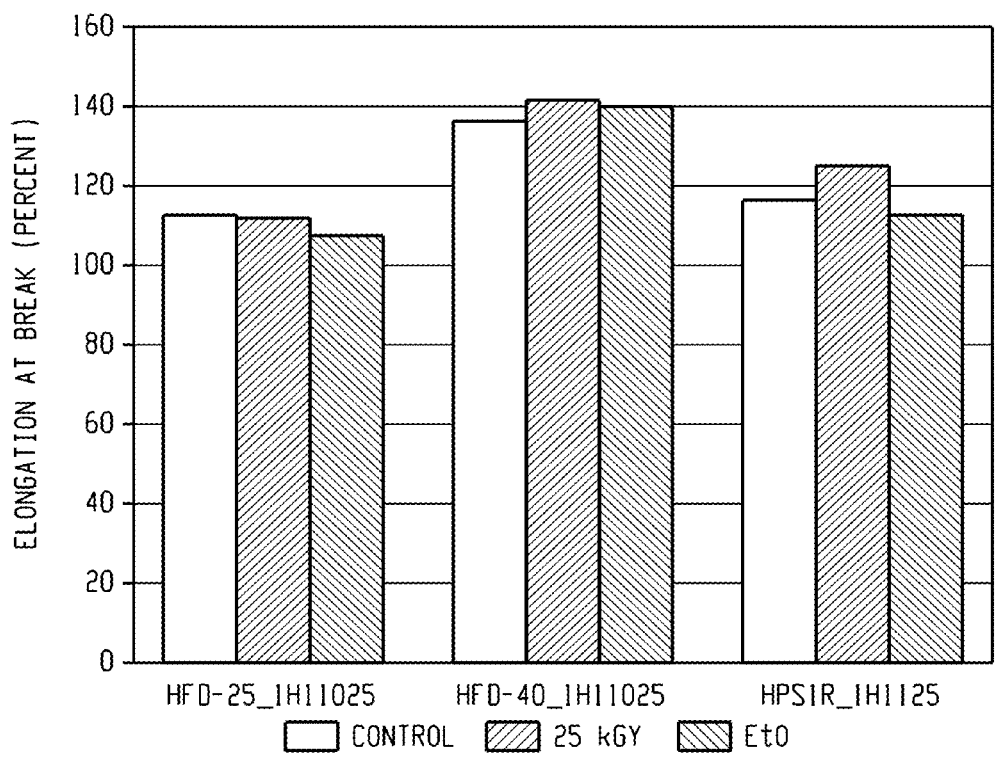
FIG. 6 is a graph illustrating the effect on elongation at break of various compositions and sterilization treatments for chip samples of 3.2 mm thickness.

FIG. 6 is a graph illustrating percent elongation at break for the various compositions after sterilization via 25 kGy gamma radiation and ethylene oxide sterilization at 3.2 mm thickness. The control is on the left, the 25 kGy in the center, and the EtO on the right for each composition. This was measured according to ASTM D638. The various values are shown in Table 8 below:

TABLE 8

| 3.2 mm chip | Control | 25 kGy | EtO |
|---|---|---|---|
| HFD-25 | 112.9 | 112.3 | 107.6 |
| HFD-40 | 136.2 | 141.6 | 140.3 |
| HPS1R | 116.2 | 124.8 | 113.0 |

No significant change in impact properties or mechanical properties was seen after exposure to sterilization treatments. In other words, the samples maintained their impact and mechanical properties.

Light transmittance and haze were also measured for samples of the HFD-25, HFD-40, and HPS1R compositions at four different thicknesses (0.65 mm, 1.2 mm, 2 mm, and 3.2 mm) and after four sterilizations (25 kGy, 50 kGy, 75 kGy, EtO). The results are listed in Table 9 and Table 10.

TABLE 9

| | Light transmittance | | | | |
|---|---|---|---|---|---|
| | Thickness (mm) | Control | 25 kGy | 50 kGy | 75 kGy | EtO |
| HFD-25 | 0.65 | 87.4 | 86.5 | 86.1 | — | — |
| HFD-40 | 0.65 | 87.2 | 86.3 | 86.0 | — | — |
| HPS1R | 0.65 | 87.5 | 86.3 | 85.6 | — | — |
| HFD-25 | 1.2 | 85.4 | 84.0 | 83.3 | — | — |
| HFD-40 | 1.2 | 85.1 | 83.7 | 83.2 | — | — |
| HPS1R | 1.2 | 85.6 | 83.5 | 82.4 | — | — |
| HFD-25 | 2 | 82.3 | 79.7 | 78.1 | — | — |
| HFD-40 | 2 | 81.9 | 79.5 | 78.1 | — | — |
| HPS1R | 2 | 82.8 | 79.0 | 77.0 | — | — |
| HFD-25 | 3.2 | 78.4 | 73.4 | 70.9 | 66.7 | 78.4 |
| HFD-40 | 3.2 | 78.1 | 73.5 | 71.2 | 67.2 | 78.1 |
| HPS1R | 3.2 | 78.5 | 72.4 | 68.8 | 63.1 | 78.5 |

TABLE 10

| | Haze | | | | |
|---|---|---|---|---|---|
| | Thickness (mm) | Control | 25 kGy | 50 kGy | 75 kGy | EtO |
| HFD-25 | 0.65 | 0.44 | 0.45 | 0.49 | — | — |
| HFD-40 | 0.65 | 0.76 | 0.69 | 0.65 | — | — |
| HPS1R | 0.65 | 0.38 | 0.34 | 0.39 | — | — |
| HFD-25 | 1.2 | 0.59 | 0.58 | 0.57 | — | — |
| HFD-40 | 1.2 | 1.09 | 1.03 | 0.98 | — | — |
| HPS1R | 1.2 | 0.39 | 0.39 | 0.40 | — | — |
| HFD-25 | 2 | 0.71 | 0.70 | 0.69 | — | — |
| HFD-40 | 2 | 1.26 | 1.24 | 1.24 | — | — |
| HPS1R | 2 | 0.46 | 0.47 | 0.48 | — | — |
| HFD-25 | 3.2 | 0.86 | 0.88 | 0.86 | 0.49 | 0.60 |
| HFD-40 | 3.2 | 1.55 | 1.55 | 1.56 | 0.82 | 0.64 |
| HPS1R | 3.2 | 0.69 | 0.65 | 0.75 | 0.57 | 1.61 |

Samples of the HFD-25, HFD-40, and HPS1R compositions at three different thicknesses (3.2 mm, 1.6 mm, and 0.8 mm) were autoclaved at 121° C. for 30 minutes and 1 hour, and then checked for warpage. FIGS. 7 to 11 show the results.

Figure 7A:
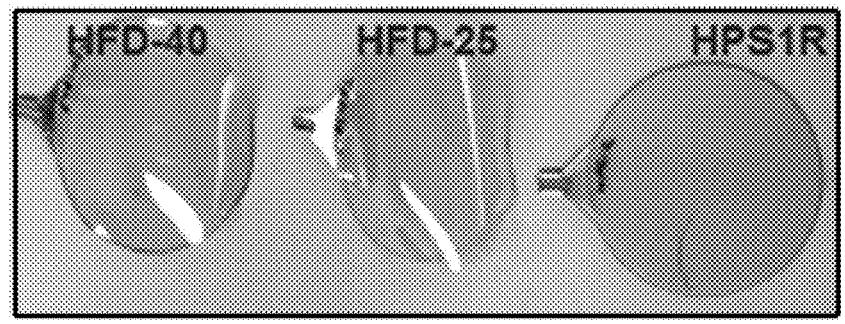
FIG. 7A is a top view of 0.8 mm thick samples after 30 minutes in an autoclave at 121° C. for two compositions of the present disclosure (HFD-40 and HFD-25) and a comparative example (HPS1R).
Figure 7B:
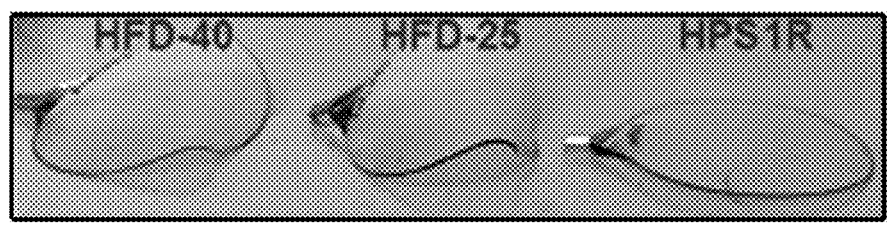
FIG. 7B is a side view of the samples shown in FIG. 7A.

FIG. 7A is a top view of the 0.8 mm thick samples after 30 minutes in an autoclave at 121° C. FIG. 7B is a side view of these samples.

Figure 8A:
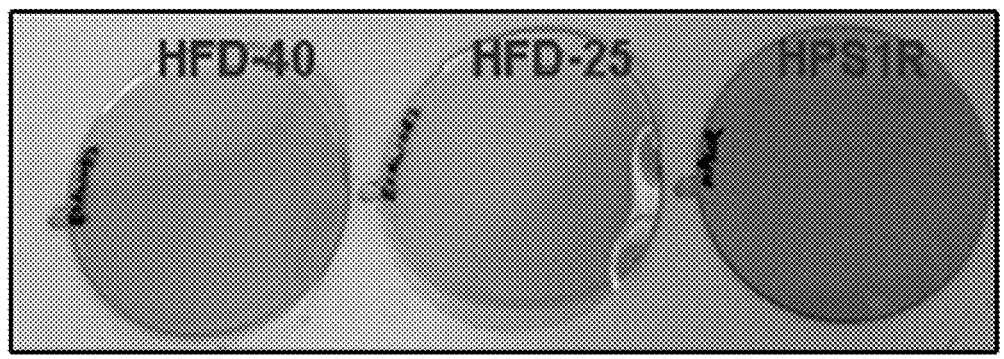
FIG. 8A is a top view of 1.6 mm thick samples after 30 minutes in an autoclave at 121° C. for two compositions of the present disclosure (HFD-40 and HFD-25) and a comparative example (HPS1R).
Figure 8B:
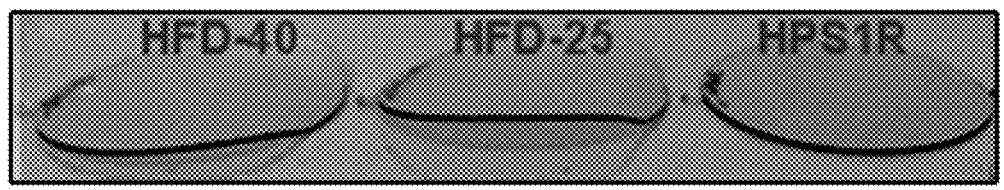
FIG. 8B is a side view of the samples shown in FIG. 8A.

FIG. 8A is a top view of the 1.6 mm thick samples after 30 minutes in an autoclave at 121° C. FIG. 8B is a side view of these samples.

Figure 9A:
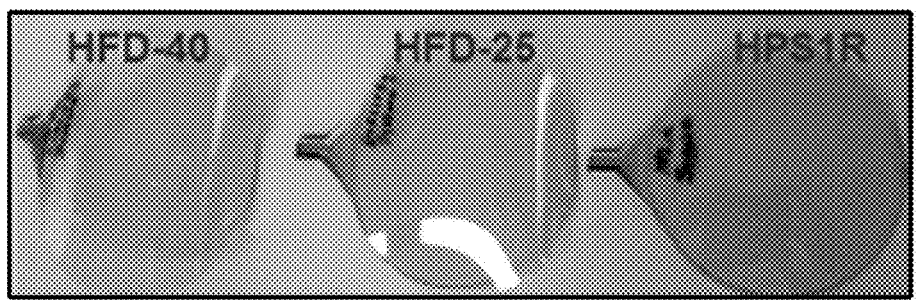
FIG. 9A is a top view of 0.8 mm thick samples after 60 minutes in an autoclave at 121° C. for two compositions of the present disclosure (HFD-40 and HFD-25) and a comparative example (HPS1R).
Figure 9B:
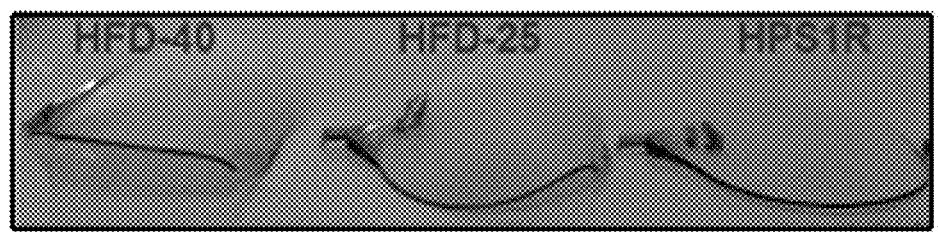
FIG. 9B is a side view of the samples shown in FIG. 9A.

FIG. 9A is a top view of the 0.8 mm thick samples after 60 minutes in an autoclave at 121° C. FIG. 9B is a side view of these samples.

Figure 10A:
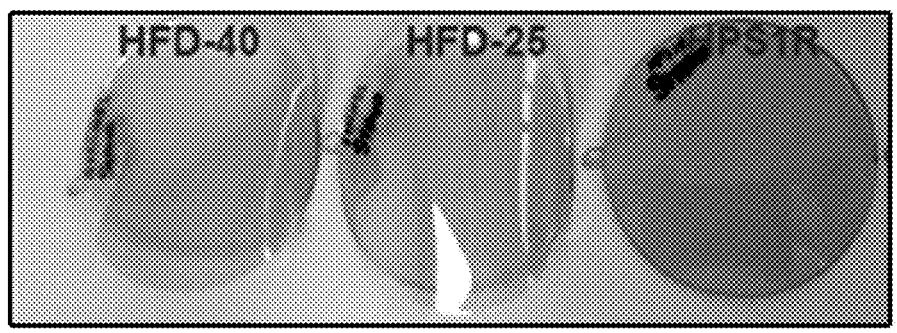
FIG. 10A is a top view of 1.6 mm thick samples after 60 minutes in an autoclave at 121° C. for two compositions of the present disclosure (HFD-40 and HFD-25) and a comparative example (HPS1R).
Figure 10B:
FIG. 10B is a side view of the samples shown in FIG. 10A.

FIG. 10A is a top view of the 1.6 mm thick samples after 60 minutes in an autoclave at 121° C. FIG. 10B is a side view of these samples.

Figure 11A:
FIG. 11A is a top view of 3.2 mm thick samples after 60 minutes in an autoclave at 121° C. for two compositions of the present disclosure (HFD-40 and HFD-25) and a comparative example (HPS1R).
Figure 11B:
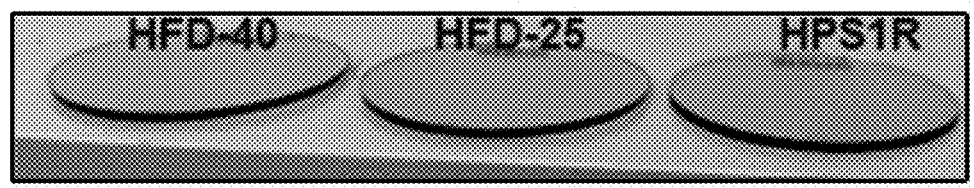
FIG. 11B is a side view of the samples shown in FIG. 11A.

FIG. 11A is a top view of the 3.2 mm thick samples after 60 minutes in an autoclave at 121° C. FIG. 11B is a side view of these samples.

The HFD-25 and HFD-40 samples showed warpage at 1.6 mm and 0.8 mm thickness after 30 minutes and 1 hour. In contrast, the HPS1R samples showed only very slight warpage at 0.8 mm thickness after 30 minutes and slight warpage for the 0.8 mm sample after 1 hour. The HSP1R had almost no warpage at 1.6 mm thickness, even after 1 hour. All three grades showed no warpage for the 3.2 mm sample. The warpage by the HFD compositions at thicknesses of less than 3.2 mm ensures single point security. In other words, a product made from the compositions of the present disclosure can be sterilized once (e.g., using gamma radiation or ethylene oxide), and then cannot be reused after a cycle of steam sterilization. This can be used to prevent reuse of medical ware/devices, which can be a serious threat to patients' health and safety.

Set forth below are embodiments of the articles disclosed herein and process for use thereof.

Embodiment 1

A medical article molded from a thermoplastic composition, comprising: at least one poly(aliphatic ester)-polycarbonate copolymer; a mold release agent; and a radiation stabilizer, wherein the thermoplastic composition has a melt flow rate of about 25 g/10 minutes or higher measured at 300° C., 1.2 kg load according to ASTM D1238; and a light transmittance of 80% or higher, and a haze of 1% or less, measured at 2.54 mm thickness according to ASTM D1003.

Embodiment 2

The article of Embodiment 1, having a wall with a thinnest thickness of 2 mm or less.

Embodiment 3

The article of Embodiment 2, wherein the wall has a thinnest thickness of 0.3 mm or less.

Embodiment 4

The article as in any of Embodiments 1-3, wherein the composition includes two poly(aliphatic ester)-polycarbonate copolymers, a first poly(aliphatic ester)-polycarbonate copolymer having a weight average molecular weight of from about 15,000 to about 25,000, and a second poly(aliphatic ester)-polycarbonate copolymer having a weight average molecular weight of 30,000 to about 40,000.

Embodiment 5

The article of Embodiment 4, wherein the weight ratio of the first poly(aliphatic ester)-polycarbonate copolymer to the second poly(aliphatic ester)-polycarbonate copolymer is from about 3:2 to about 20:1.

Embodiment 6

The article as in any of Embodiments 4-5, wherein the first poly(aliphatic ester)-polycarbonate copolymer contains about 6.0 mole % sebacic acid, and the second poly(aliphatic ester)-polycarbonate copolymer contains about 8.25 mole % sebacic acid.

Embodiment 7

The article as in any of Embodiments 1-6, wherein the at least one poly(aliphatic ester)-polycarbonate copolymer is derived from bisphenol-A and sebacic acid.

Embodiment 8

The article as in any of Embodiments 1-7, wherein the at least one poly(aliphatic ester)-polycarbonate copolymer has a biocontent of from about 4 wt % to about 10 wt %, measured according to ASTM D6866.

Embodiment 9

The article as in any of Embodiments 1-8, wherein the article has a heat distortion temperature of 120° C. or less when measured at 1.82 MPa, 3.2 mm thickness according to ASTM D648, such that the article distorts when autoclaved.

Embodiment 10

The article as in any of Embodiments 1-8, wherein the article has a heat distortion temperature of 121° C. or higher when measured at 1.82 MPa, 3.2 mm thickness according to ASTM D648.

Embodiment 11

The article as in any of Embodiments 1-10, wherein the article has a peak instrumented impact energy of 60 J or higher, when measured at 23° C. according to ASTM D3763.

Embodiment 12

The article as in any of Embodiments 1-11, wherein the article has a notched Izod impact strength (INI) of 680 J/m or higher, when measured at 23° C. according to ASTM D256.

Embodiment 13

The article as in any of Embodiments 1-12, wherein the article has a notched Izod impact strength (INI) of 450 J/m or higher, when measured at 0° C. according to ASTM D256.

Embodiment 14

The article as in any of Embodiments 1-13, wherein the article has a notched Izod impact strength (INI) of 680 J/m or higher when measured at 23° C., and a notched Izod impact strength (INI) of 450 J/m or higher when measured at 0° C., according to ASTM D256.

Embodiment 15

The article as in any of Embodiments 1-14, wherein the article has a notched Izod impact strength (INI) of 750 J/m or higher when measured at 23° C., and a notched Izod impact strength (INI) of 750 J/m or higher when measured at 0° C., according to ASTM D256.

Embodiment 16

The article as in any of Embodiments 1-15, wherein the radiation stabilizer is hexylene glycol.

Embodiment 17

The article as in any of Embodiments 1-16, wherein the mold release agent is a polyalphaolefin.

Embodiment 18

The article as in any of Embodiments 1-17, wherein the thermoplastic composition further includes an epoxy resin.

Embodiment 19

The article as in any of Embodiments 1-18, wherein the medical article is non-implantable.

Embodiment 20

The article as in any of Embodiments 1-19, wherein the medical article is a blood bowl, disposable hypodermic syringe, needle shield, tubing/line, connector, needle wing, cannula, safety barrel, filter medium, sharps container, tray, injectable drug vial, prescription pill vial, inhaler part, IV drug or saline bag, blood bag, transfusion/retransfusion bag, irrigation solution bottle, fluid replacement bottle, nose spray bottle, packaging blister, surgical gown, isolation gown, isolation drape, sterilization wrap, or face mask.

Embodiment 21

The article as in any of Embodiments 1-19, wherein the medical article is a housing for a medical device.

Embodiment 22

A medical article molded from a thermoplastic composition comprising: a first poly(aliphatic ester)-polycarbonate copolymer having a weight average molecular weight of from about 15,000 to about 25,000; a second poly(aliphatic ester)-polycarbonate copolymer having a weight average molecular weight of 30,000 to about 40,000; a mold release agent; a radiation stabilizer; and an epoxy resin; wherein the weight ratio of the first poly(aliphatic ester)-polycarbonate copolymer to the second poly(aliphatic ester)-polycarbonate copolymer is about 3:1; and wherein the thermoplastic composition has a melt flow rate of about 25 g/10 minutes or higher when measured at 300° C., 1.2 kg load according to ASTM D1238; a light transmittance of 80% or higher, and a haze of 1% or less, measured at 2.54 mm thickness according to ASTM D1003; a heat distortion temperature of 120° C. or less when measured at 1.82 MPa, 3.2 mm thickness according to ASTM D648; a notched Izod impact strength (INI) of 750 J/m or higher when measured at 23° C., and a notched Izod impact strength (INI) of 750 J/m or higher when measured at 0° C., according to ASTM D256.

Embodiment 23

The article of Embodiment 22, wherein the first and second poly(aliphatic ester)-polycarbonate copolymers are each derived from bisphenol-A and sebacic acid.

Embodiment 24

The article as in any of Embodiments 22-23, wherein the first poly(aliphatic ester)-polycarbonate copolymer contains about 6.0 mole % sebacic acid, and the second poly(aliphatic ester)-polycarbonate copolymer contains about 8.25 mole % sebacic acid.

Embodiment 25

The article as in any of Embodiments 22-24, wherein the radiation stabilizer is hexylene glycol and the mold release agent is a polyalphaolefin.

Embodiment 26

The article as in any of Embodiments 22-25, wherein the composition contains about 0.3 phr of the mold release agent, about 0.1 phr of the radiation stabilizer, and about 0.1 phr of the epoxy resin.

Embodiment 27

A medical article molded from a thermoplastic composition comprising: a first poly(aliphatic ester)-polycarbonate copolymer having a weight average molecular weight of from about 15,000 to about 25,000; a second poly(aliphatic ester)-polycarbonate copolymer having a weight average molecular weight of 30,000 to about 40,000; a mold release agent; a radiation stabilizer; and an epoxy resin; wherein the weight ratio of the first poly(aliphatic ester)-polycarbonate copolymer to the second poly(aliphatic ester)-polycarbonate copolymer is about 19:1; and wherein the thermoplastic composition has a melt flow rate of about 40 g/10 minutes or higher when measured at 300° C., 1.2 kg load according to ASTM D1238; a light transmittance of 80% or higher, and a haze of 1% or less, measured at 2.54 mm thickness according to ASTM D1003; a heat distortion temperature of 120° C. or less when measured at 1.82 MPa, 3.2 mm thickness according to ASTM D648; a notched Izod impact strength (INI) of 680 J/m or higher when measured at 23° C., and a notched Izod impact strength (INI) of 450 J/m or higher when measured at 0° C., according to ASTM D256.

Embodiment 28

The article of Embodiment 27, wherein the first and second poly(aliphatic ester)-polycarbonate copolymers are each derived from bisphenol-A and sebacic acid.

Embodiment 29

The article as in any of Embodiments 27-28, wherein the first poly(aliphatic ester)-polycarbonate copolymer contains about 6.0 mole % sebacic acid, and the second poly(aliphatic ester)-polycarbonate copolymer contains about 8.25 mole % sebacic acid.

Embodiment 30

The article as in any of Embodiments 27-29, wherein the radiation stabilizer is hexylene glycol and the mold release agent is a polyalphaolefin.

Embodiment 31

The article as in any of Embodiments 27-30, wherein the composition contains about 0.3 phr of the mold release agent, about 0.1 phr of the radiation stabilizer, and about 0.1 phr of the epoxy resin.

Embodiment 32

The article as in any of Embodiments 1-31, wherein the article distorts when autoclaved.

Embodiment 33

The article as in any of Embodiments 1-32, wherein the composition has a delta YI of 3 or less when measured at least 48 hours after exposure to 50 kGy of gamma radiation at 0.65 mm thickness.

Embodiment 34

The article as in any of Embodiments 1-33, wherein the composition has a multiaxial impact strength of at least 60 J when measured at least 48 hours after exposure to 50 kGy of gamma radiation at 3.2 mm thickness.

Embodiment 35

The article as in any of Embodiments 1-34, wherein the composition has a tensile modulus of at least 2300 MPa when measured at least 48 hours after exposure to 25 kGy of gamma radiation at 3.2 mm thickness.

Embodiment 36

The article as in any of Embodiments 1-35, wherein the composition has a % elongation at break of at least 100% when measured at least 48 hours after exposure to 25 kGy of gamma radiation at 3.2 mm thickness.

Embodiment 37

A process for preventing the reuse of a medical article molded from a thermoplastic composition, comprising: forming the medical article from a thermoplastic composition comprising: at least one poly(aliphatic ester)-polycarbonate copolymer; a mold release agent; and a radiation stabilizer; wherein the thermoplastic composition has a melt flow rate of about 25 g/10 minutes or higher measured at 300° C., 1.2 kg load according to ASTM D1238; and a light transmittance of 80% or higher, and a haze of 1% or less, measured at 2.54 mm thickness according to ASTM D1003; and wherein the article has a heat distortion temperature of 120° C. or less when measured at 1.82 MPa, 3.2 mm thickness according to ASTM D648.

Embodiment 38

The process of Embodiment 37, wherein preventing the reuse means the integrity of the medical article is not maintained for further use after the medical article is subjected to sterilization or autoclaving.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A medical article molded from a thermoplastic composition, comprising:
   at least one poly(aliphatic ester)-polycarbonate copolymer;
   a mold release agent; and
   a radiation stabilizer,
   wherein the thermoplastic composition has a melt flow rate of about 25 g/10 minutes or higher measured at 300° C., 1.2 kg load according to ASTM D1238; and a light transmittance of 80% or higher, and a haze of 1% or less, measured at 2.54 mm thickness according to ASTM D1003.

2. The article as in claim 1, wherein the at least one poly(aliphatic ester)-polycarbonate copolymer is derived from bisphenol-A and sebacic acid.

3. The article of claim 1, wherein the at least one poly(aliphatic ester)-polycarbonate copolymer has a biocontent of from about 4 wt % to about 10 wt %, measured according to ASTM D6866.

4. The article of claim 1, wherein the radiation stabilizer is hexylene glycol.

5. The article of claim 1, wherein the mold release agent is a polyalphaolefin.

6. The article of claim 1, wherein the thermoplastic composition further includes an epoxy resin.

7. The article of claim 1, wherein the medical article is non-implantable.

8. The article of claim 1, wherein the medical article is a housing for a medical device.

9. The article of claim 1, wherein the medical article is a blood bowl, disposable hypodermic syringe, needle shield, tubing/line, connector, needle wing, cannula, safety barrel, filter medium, sharps container, tray, injectable drug vial, prescription pill vial, inhaler part, IV drug or saline bag, blood bag, transfusion/retransfusion bag, irrigation solution bottle, fluid replacement bottle, nose spray bottle, packaging blister, surgical gown, isolation gown, isolation drape, sterilization wrap, or face mask.

10. The article of claim 1, having a wall with a thinnest thickness of 2 mm or less.

11. The article of claim 10, wherein the wall has a thinnest thickness of 0.3 mm or less.

12. The article of claim 1, wherein the composition includes two poly(aliphatic ester)-polycarbonate copolymers, a first poly(aliphatic ester)-polycarbonate copolymer having a weight average molecular weight of from about 15,000 to about 25,000, and a second poly(aliphatic ester)-polycarbonate copolymer having a weight average molecular weight of 30,000 to about 40,000.

13. The article of claim 12, wherein the weight ratio of the first poly(aliphatic ester)-polycarbonate copolymer to the second poly(aliphatic ester)-polycarbonate copolymer is from about 3:2 to about 20:1.

14. The article of claim 12, wherein the first poly(aliphatic ester)-polycarbonate copolymer contains about 6.0 mole % sebacic acid, and the second poly(aliphatic ester)-polycarbonate copolymer contains about 8.25 mole % sebacic acid.

15. The article of claim 12, further comprising an epoxy resin; and
   wherein the weight ratio of the first poly(aliphatic ester)-polycarbonate copolymer to the second poly(aliphatic ester)-polycarbonate copolymer is about 19:1; and
   wherein the thermoplastic composition has a melt flow rate of about 40 g/10 minutes or higher when measured at 300° C., 1.2 kg load according to ASTM D1238; a light transmittance of 80% or higher, and a haze of 1% or less, measured at 2.54 mm thickness according to ASTM D1003; a heat distortion temperature of 120° C. or less when measured at 1.82 MPa, 3.2 mm thickness according to ASTM D648; a notched Izod impact strength (INI) of 680 J/m or higher when measured at 23° C., and a notched Izod impact strength (INI) of 450 J/m or higher when measured at 0° C., according to ASTM D256.

16. A medical article molded from a thermoplastic composition comprising:
   a first poly(aliphatic ester)-polycarbonate copolymer having a weight average molecular weight of from about 15,000 to about 25,000;
   a second poly(aliphatic ester)-polycarbonate copolymer having a weight average molecular weight of 30,000 to about 40,000;
   a mold release agent;
   a radiation stabilizer; and
   an epoxy resin;
   wherein the weight ratio of the first poly(aliphatic ester)-polycarbonate copolymer to the second poly(aliphatic ester)-polycarbonate copolymer is about 3:1; and
   wherein the thermoplastic composition has a melt flow rate of about 25 g/10 minutes or higher when measured at 300° C., 1.2 kg load according to ASTM D1238; a light transmittance of 80% or higher, and a haze of 1% or less, measured at 2.54 mm thickness according to ASTM D1003; a heat distortion temperature of 120° C. or less when measured at 1.82 MPa, 3.2 mm thickness according to ASTM D648; a notched Izod impact strength (INI) of 750 J/m or higher when measured at 23° C., and a notched Izod impact strength (INI) of 750 J/m or higher when measured at 0° C., according to ASTM D256.

17. The article of claim 16, wherein the first and second poly(aliphatic ester)-polycarbonate copolymers are each derived from bisphenol-A and sebacic acid.

18. The article of claim 16, wherein the first poly(aliphatic ester)-polycarbonate copolymer contains about 6.0 mole % sebacic acid, and the second poly(aliphatic ester)-polycarbonate copolymer contains about 8.25 mole % sebacic acid.

19. The article of claim 16, wherein the radiation stabilizer is hexylene glycol and the mold release agent is a polyalphaolefin.

20. A process for preventing the reuse of a medical article molded from a thermoplastic composition, comprising:
   forming the medical article from a thermoplastic composition comprising:
   at least one poly(aliphatic ester)-polycarbonate copolymer;
   a mold release agent; and
   a radiation stabilizer;
   wherein the thermoplastic composition has a melt flow rate of about 25 g/10 minutes or higher measured at 300° C., 1.2 kg load according to ASTM D1238; and a light transmittance of 80% or higher, and a haze of 1% or less, measured at 2.54 mm thickness according to ASTM D1003; and wherein the article has a heat distortion temperature of 120° C. or less when measured at 1.82 MPa, 3.2 mm thickness according to ASTM D648.

\* \* \* \* \*